US009849165B2

(12) United States Patent
Cashman

(10) Patent No.: US 9,849,165 B2
(45) Date of Patent: *Dec. 26, 2017

(54) OLIGOMER-SPECIFIC AMYLOID BETA EPITOPE AND ANTIBODIES

(71) Applicant: The University of British Columbia, Vancouver (CA)

(72) Inventor: Neil R. Cashman, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/971,529

(22) Filed: Dec. 16, 2015

(65) Prior Publication Data

US 2016/0228522 A1    Aug. 11, 2016

Related U.S. Application Data

(62) Division of application No. 13/582,308, filed as application No. PCT/CA2011/000238 on Mar. 3, 2011, now Pat. No. 9,216,217.

(60) Provisional application No. 61/310,167, filed on Mar. 3, 2010.

(51) Int. Cl.

| A61K 39/00 | (2006.01) |
|---|---|
| C07K 14/47 | (2006.01) |
| C07K 16/18 | (2006.01) |
| G01N 33/68 | (2006.01) |
| C07K 7/06 | (2006.01) |
| A61K 39/395 | (2006.01) |
| A61K 45/06 | (2006.01) |

(52) U.S. Cl.
CPC ...... *A61K 39/0005* (2013.01); *A61K 39/3955* (2013.01); *A61K 45/06* (2013.01); *C07K 7/06* (2013.01); *C07K 14/4711* (2013.01); *C07K 16/18* (2013.01); *G01N 33/6896* (2013.01); *A61K 39/00* (2013.01); *A61K 2039/58* (2013.01); *C07K 2317/34* (2013.01); *G01N 2333/4709* (2013.01)

(58) Field of Classification Search
CPC ....... G01N 33/6896; G01N 2333/4709; A61K 39/3955; A61K 39/0005; A61K 45/06; A61K 47/6811; A61K 2039/58; A61K 39/00; C07K 14/4711; C07K 7/64; C07K 7/06; C07K 16/18; C07K 2317/34; C07K 11/02

See application file for complete search history.

(56) References Cited

U.S. PATENT DOCUMENTS

| 4,816,397 A | 3/1989 | Boss et al. |
|---|---|---|
| 4,816,567 A | 3/1989 | Cabilly et al. |
| 6,660,843 B1 | 12/2003 | Feige et al. |
| 6,750,324 B1 | 6/2004 | Schenk et al. |
| 6,972,127 B2 * | 12/2005 | Schenk ............... A61K 9/2031 424/1.57 |
| 7,569,541 B2 | 8/2009 | Pluschke et al. |
| 2004/0014100 A1 | 1/2004 | Lorenz et al. |
| 2009/0215172 A1 | 8/2009 | Schmidt et al. |
| 2010/0137559 A1 | 6/2010 | Tovi et al. |
| 2010/0240856 A1 | 9/2010 | Tovi et al. |
| 2011/0182928 A1 | 7/2011 | Hoogerhout et al. |
| 2013/0089537 A1 | 4/2013 | Goure et al. |
| 2014/0314773 A1 | 10/2014 | Cashman et al. |

FOREIGN PATENT DOCUMENTS

| EP | 0171496 A2 | 2/1986 |
|---|---|---|
| EP | 0173494 A2 | 3/1986 |
| EP | 0239400 A2 | 9/1987 |
| JP | 2007/145863 A | 6/2007 |
| JP | 2009/500639 A | 1/2009 |
| JP | 2009/543575 A | 12/2009 |
| WO | 90/07861 A1 | 7/1990 |
| WO | 92/06193 A1 | 4/1992 |
| WO | 97/37228 A1 | 10/1997 |
| WO | 99/25044 A1 | 5/1999 |
| WO | 01/92466 A2 | 12/2001 |
| WO | 2007/007327 A2 | 1/2007 |
| WO | 2008/010101 A2 | 1/2008 |
| WO | 2010/0002251 A1 | 1/2010 |
| WO | 2010/010469 A2 | 1/2010 |
| WO | 2010/011947 A2 | 1/2010 |

(Continued)

OTHER PUBLICATIONS

Potter P.E. "Investigational Medications for Treatment of Patients With Alzheimer Disease" J. Am. Osteopath. Assoc. Sep. 2010 (Sep. 2010), 110 (9 Suppl 8):827-36).
Howard, Gary C. et al. (Eds.) Basic Methods in Antibody Production and Characterization, 2001, p. 52.
Maftei, Madalina et al. Increased levels of antigen-bound B-amyloid autoantibodies in serum and cerebrospinal fluid of Alzheimer's disease patients. PLoS On. Jul. 18, 2013;8(7):e68996.
Rudikoff, Stuart et al.,Rudicoff S. et al., Single amino acid substitution altering antibody-binding specificity, Proc. Nat. Acad. Sci. USA Immunology, 1982, 79: abstract in p. 1979.
Andreu et al., "Formation of Disulfide Bonds in Synthetic Peptides and Proteins", Methods in Molecular Biology—Peptide Synthesis Protocols—Chapter 7, 1994, pp. 91-169, vol. 35.

(Continued)

*Primary Examiner* — Gregory S Emch
(74) *Attorney, Agent, or Firm* — Bereskin & Parr LLP; Carmela De Luca

(57) ABSTRACT

A novel constrained peptide epitope derived from Aβ, related antibody compositions and methods of use. An isolated antibody that specifically binds to a cyclic peptide comprising the conformational epitope corresponding to a solvent-exposed, antibody accessible knuckle region of oligomeric Aβ is described. An antigenic peptide comprising an epitope having a constrained cyclic configuration, corresponding to a solvent-exposed, antibody accessible knuckle region of oligomeric Aβ is also described. Methods of treating, preventing, and diagnosing Alzheimer's disease are also described.

12 Claims, 13 Drawing Sheets

(56) References Cited

FOREIGN PATENT DOCUMENTS

| WO | 2010/075280 A2 | 7/2010 |
| WO | 2011/100292 A1 | 8/2011 |
| WO | 2011/106885 A1 | 9/2011 |
| WO | 2013/071267 A1 | 5/2013 |

OTHER PUBLICATIONS

Bourne et al., "A Convenient Method for Synthesis of Cyclic Peptide Libraries", Methods in Molecular Biology—Peptide Synthesis and Applications—Chapter 10, 2005, pp. 151-165, vol. 298.
De Felice et al., "A-beta Oligomers Induce Neuronal Oxidative Stress Through an N-Methyl-D-Aspartate Receptor-Dependent Mechanism That is Blocked by the Alzheimer Drug Memantine", Journal of Biological Chemistry, Apr. 13, 2007, vol. 282, No. 15.
Henikoff et al., "Amino Acid Substitution Matrices from Protein Block", Proceedings of the National Academy of Sciences—United States of America, Nov. 1992, pp. 10915-10919, vol. 89.
Huse et al., "Generation of a Large Combinatorial Library of the Immunoglobulin Repertoire in Phage Lambda", Science, Dec. 8, 1989, pp. 1275-1281.
Jung et al., "A Radiotracer for Mapping Cholinergic Neurons of the Brain", Journal of Medicinal Chemistry, 1990, pp. 2065-2068, vol. 33.
Khosravani et al., "Cellular Prion Protein Null Mice Display Normal AMPA Receptor Mediated Long Term Depression", Prion, 2008, pp. 48-50, vol. 2, Issue 2.
Kozbor et al., "The Production of Monoclonal Antibodies from Human Lymphocytes", Immunology Today, 1983, pp. 72-79, vol. 4 No. 3.
Lefebvre-Roque et al., "Toxic Effects of Intracerebral PrP Antibody Administration During the Course of BSE Infection in Mice", Prion, 2007, pp. 198-206, vol. 1, Issue 3.
Nimmrich et al., "Amyloid Beta Oligomers (Abeta(1-42) Globulomer) Suppress Spontaneous Synaptic Activity by Inhibition of P/Q-Type Calcium Currents", The Journal of Neuroscience, Jan. 23, 2008, pp. 788-797, vol. 28, No. 4.
Olsson et al., "Human-Human Monoclonal Antibody-Producing Hybridomas: Technical Aspects", Methods in Enzymology, 1983, pp. 3-16, vol. 92.
Paramithiotis et al., "A Prion Protein Epitope Selective for the Pathologically Misfolded Conformation", Nature Medicine, Jul. 2003, pp. 893-899, vol. 9 No. 7.
Rakhit et al., "An Immunological Epitope Selective for Pathological Monomer/Misfolded SOD1 in ALS", Nature Medicine, Jun. 2007, pp. 754-759, vol. 13 No. 6.
Rauk, "The Chemistry of Alzheimer's Disease", Chemical Society Reviews, 2009, pp. 2698-2715, vol. 38 (First published as an Advance Article on the web Jun. 18, 2009).
Sawaya et al., "Atomic Structures of Amyloid Cross-beta Spines Reveal Varied Steric Zippers", Nature, May 24, 2007, pp. 453-457, vol. 447.
Solfororsi et al., "Cross-Linking Cellular Prion Protein Triggers Neuronal Apoptosis in Vivo", Science, Mar. 5, 2004, pp. 1514-1516, vol. 303.
Takeda et al., "Constructions of Chimaeric Processed Immunoglobulin Genes Containing Mouse Variable and Human Constant Region Sequences", Nature, Apr. 1985, pp. 452-454, vol. 314.
Teng et al., "Construction and Testing of Mouse-Human Heteromyelomas for Human Monoclonal Antibody Production", Proceedings of the National Academy of Science—United States of America, Dec. 1983, pp. 7308-7312, vol. 80.
Zhao et al., "Insulin Resistance and Amyloidogenesis as Common Molecular Foundation for Type 2 Diabetes and Alzheimer's Disease", Biochimica et Biophysica Acta, 2009, pp. 482-496, vol. 1792 (Available online Nov. 5, 2008).
Balducci et al., "Synthetic Amyloid-b Oligomers Impair Long-Term Memory Independently of Cellular Prion Protein", Proceedings of the National Academy of Sciences, Feb. 2010, pp. 2295-2300, vol. 107 No. 5.
Broytman et al., "Anti-Abeta: The Good, the Bad, and the Unforeseen", Journal of Neuroscience Research, 2004, pp. 301-306, vol. 75.
Frisardi et al., "Towards Disease-Modifying Treatment of Alzheimer's Disease: Drugs Targeting Beta-Amyloid", Current Alzheimer Research, Feb. 2010, pp. 40-55, vol. 7.
Fukuchi et al., "Amelioration of Amyloid Load by Anti-Abeta Single-Chain Antibody in Alzheimer Mouse Model", Biochem Biophys Res Commun, May 26, 2006, pp. 79-86, vol. 344.
Gelinas et al., "Immunotherapy for Alzheimer's Disease", Proceedings of the National Academy of Sciences, Oct. 2004, pp. 14657-14662, vol. 101 Suppl. 2.
Goni et al., "New Directions Towards Safer and Effective Vaccines for Alzheimer's Disease", Current Opinion in Molecular Therapeutics, 2005, pp. 17-23, vol. 7 No. 1.
Hoogerhout et al., "A Cyclic Undecamer Peptide Mimics a Turn in Folded Alzheimer Amyloid beta and Elicits Antibodies Against Oligomeric and Fibrillar Amyloid and Plaques", PLOS One, Apr. 19, 2011, pp. 1-6, vol. 6 No. 4.
International Search Report and Written Opinion for PCT/US2012/064722 dated Mar. 15, 2013.
Jung et al., "Alzheimer's Beta-Amyloid Precursor Protein is Expressed on the Surface of Immediately Ex Vivo Brain Cells: A Flow Cytometric Study", Journal of Neuroscience Research, 1996, pp. 336-348, vol. 46.
Jung et al., "Beta-Amyloid Precursor Protein is Detectable on Monocytes and is Increased in Alzheimer's Disease", Neurobiology of Aging, 1999, pp. 249-257.
Klyubin et al., "Amyloid beta Protein Immunotherapy Neutralizes Ab Oligomers that Disrupt Synaptic Plasticity In Vivo", Nature Medicine, May 2005, pp. 556-561, vol. 11 No. 5.
Lacor et al., "Abeta Oligomer-Induced Aberrations in Synapse Composition, Shape, and Density Provide a Molecular Basis for Loss of Connectivity in Alzheimer's Disease", The Journal of Neuroscience, Jan. 24, 2007, pp. 796-807, vol. 27 No. 4.
Lambert et al., "Monoclonal Antibodies that Target Pathological Assemblies of Ab", Journal of Neurochemistry, 2007, pp. 23-35, vol. 100.
Lauren et al., "Cellular Prion Protein Mediates Impairment of Synaptic Plasticity by Amyloid-b Oligomers", Nature, Feb. 2009, pp. 1128-1134, vol. 457.
Lesne et al., "A Specific Amyloid-beta Protein Assembly in the Brain Impairs Memory", Nature, Mar. 2006, pp. 352-357, vol. 440.
Luhrs et al., "3D Structure of Alzheimer's Amyloid-b(1-42) Fibrils", Proceedings of the National Academy of Sciences, pp. 17342-17347, Nov. 2005, vol. 102 No. 48.
Mathews et al., "Setback for an Alzheimer's Disease Vaccine: Lessons Learned", Neurology, 2003, pp. 7-8, vol. 61.
Mileusnic et al., "Amyloid Precursor Protein from Synaptic Plasticity to Alzheimer's Disease", Annals of the New York Academy of Sciences, 2005, pp. 149-165, vol. 1048.
Mileusnic et al., "APP is Required During an Early Phase of Memory Formation", European Journal of Neuroscience, 2000, pp. 4487-4495, vol. 12.
Morimoto et al., "Involvement of Amyloid Precursor Protein in Functional Synapse Formation in Cultured Kippocampal Neurone", Journal of Neuroscience Research, 1998, pp. 185-195, vol. 51.
Nitsch, "Targeting Beta-Amyloid Pathology in Alzheimer's Disease with Abeta Immunotherapy", Neurotherapeutics, Jul. 2008, pp. 415-420, vol. 5.
Olofsson et al., "The Solvent Protection of Alzheimer Amyloid-B-(1-42) Fibrils as Determined by Solutions NMR Spectroscopy", The Journal of Biological Chemistry, 2006, pp. 477-483, vol. 281.
Rauk, "Why is the Amyloid Beta Peptide of Alzheimer's Disease Neurotoxic?", Dalton Transactions, 2008, pp. 1273-1282.
Robinson et al., Lessons from the AN 1792 Alzheimer Vaccine: Lest We Forget, Neurobiology of Aging, 2004, pp. 609-615.

(56) References Cited

OTHER PUBLICATIONS

Ronicke et al., "Abeta Mediated Diminution of MTT Reduction—An Artefact of Single Cell Culture?", PLoS One, Sep. 2008, 9 pages, vol. 3 Issue 9, e3236.

Selkoe, "Soluble Oligomers of the Amyloid b-Protein Impair Synaptic Plasticity and Behavior", Behavioural Brain Research, 2008, pp. 106-113.

Shankar et al., "Amyloid-beta Protein Dimers Isolated Directly from Alzheimer's Brains Impair Synaptic Plasticity and Memory", Nature Medicine, Aug. 2008, pp. 837-842, vol. 14 No. 8.

Walsh et al., "Naturally Secreted Oligomers of Amyloid b Protein Potently Inhibit Hippocampal Long-Term Potentiation In Vivo", Letters to Nature, Apr. 2002, pp. 535-539, vol. 416.

Wang et al., "Soluble Oligomers of b Amyloid (1-42) Inhibit Long-Term Potentiation But Not Long-Term Depression in Rat Dentate Gyrus", Brain Research, 2002, pp. 133-140.

Supplementary European Search Report issued in European Application No. EP11750124 dated Jun. 20, 2013.

International Search Report and Written Opinion issued in PCT/CA2011/000238 dated May 19, 2011.

\* cited by examiner

SEQ ID NO: 4
H-IgH1st3prime 489 48 426 0.05

NNNNNNNNNTNNNNNNNNNNNANNNNNNNNNANNATAGCCCTTGNNNNGCATCCCAGGGTCACCAT
GGAGTTAGTTTGGGCAGCAGATCCAGGGGCCAGTGGATAGACAGATGGGGGTGTCGTTTTGGCTGAGGA
GACTGTGAGAGTGGTGCCTTGGCCCCAGTAGTGAGCCTCGTAATCCATCCTTGCACAGAAATAGACCGCA
GAGTCCTCAGAGGTCAATCTGCTGAGCTGCATGTAGGCTGTGCTGGAGGATTTGTCTGCAGTCAGTGTGG
CCTTGCCCTTGAACTTCTCATTGTACTTAGTATTAACATTTCCAGGATAAATCCATCCAATCCACTCAAGTCC
CTGTCCAGGCCTGTGTATCACCCACTGTATATAGTAGCTTGTGAATATGTAGCCAGAAGCCTTGCAGGATA
TCCTCACTGAAGCCCCAGGCTTCACCAGCTCAGGTCCAGACTCCTGCAGCTGCACCTCNNAATTNNNNNN
N

SEQ ID NO: 5
H-IgH1st5prime 486 16 450 0.05

NNNNNNNNTGGNGANCCTGGGGCTTCNGTGAGGANATCCTGCAAGGCTTCTGGCTACATATTCACAAGC
TACTATATACAGTGGGTGATACACAGGCCTGGACAGGGACTTGAGTGGATTGGATGGATTTATCCTGGAA
ATGTTAATACTAAGTACAATGAGAAGTTCAAGGGCAAGGCCACACTGACTGCAGACAAATCCTCCAGCAC
AGCCTACATGCAGCTCAGCAGATTGACCTCTGAGGACTCTGCGGTCTATTTCTGTGCAAGGATGGATTACG
AGGCTCACTACTGGGGCCAAGGCACCACTCTCACAGTCTCCTCAGCCAAAACGACACCCCCATCTGTCTAT
CCACTGGCCCCTGGATCTGCTGCCCAAACTAACTCCATGGTGACCCTGGGATGCCTGGTCAAGGGCTATTT
CCCTGAGCCAGTGACAGTGACCTGGAACTCTGGATCCCTGTCCAGCGGTGTNNNNAACCTTNNN

SEQ ID NO: 6
3prime Kappa

NNNNNNNNNNNGTTTNATTNNNGCTTGGTGCCTCCTCCGAACGTCCGAGGATAATTATGATATTGTAGA
CAGTTGTTGTCTGCACAATCTTCTCACTCAAGGGTGCTGATGGGGAGAGAATAATCTGACACCCACCTACT
GCCACTGAGCCTTTTTGGGACACCTCAATCTTGAGTGGATGCGGCGTAAATCANGCGTTTAATAGTTCCGT
CTGGTTTCTGCTGAAGCCAGGTTAAGTAACCACTAATTTCCTGACTTGCCCGACGAGTGAGACTGACTCTTT
CTCCCTCAGAGGCAGATAAGGAGGATGGANACTGGGTCATCTGGATGTCACATCTGGTACCTGGNAACC
NGANNCNCAAAAAANCAGCAA

SEQ ID NO: 7
5prime Kappa

NNNNNNNNNNNNNNNNNCNNGTCNNNTCCTCCTTATCTGCCTCTCTGGGAGAAAAAGTCCGTCTCAC
TTGTCGGGCAAGTCNAGAAATTAGTGCTTACTTAACCTGGCTTCAGCAGAGACCCCATGGAACTATTAGAC
GCCCGATCTAACCCCCATCCTCTTTAGATTCTGGTGTCCCAAAAAGGGTCCCTGCCAGGATGTCTGGGTCA
GATTATTCTATCAACATCACCATCCTTGAGTCTGAAGATTATGAAGACGATGCCTGTCTACAATATGGTAAT
TATCCTCGGAAGTTCAGTGGAGGCAACGAGCTAGAAATCTAACAGGCTGATGCTGCAACAACTGTATCCA
TCTTCCCACCATCACACCATCA

Fig. 15

SEQUENCE LISTING

```
<160> NUMBER OF SEQ ID NOS: 8

<210> SEQ ID NO 1
<211> LENGTH: 5
<212> TYPE: PRT
<213> ORGANISM: artificial sequence
<220> FEATURE:
```

<223> OTHER INFORMATION: peptide epitope

<400> SEQUENCE: 1

Gly Ser Asn Lys Gly
1               5

<210> SEQ ID NO 2
<211> LENGTH: 6
<212> TYPE: PRT
<213> ORGANISM: artificial sequence
<220> FEATURE:
<223> OTHER INFORMATION: peptide epitope

<400> SEQUENCE: 2

Phe Arg His Asp Ser Gly
1               5

<210> SEQ ID NO 3
<211> LENGTH: 8
<212> TYPE: PRT
<213> ORGANISM: artificial sequence
<220> FEATURE:
<223> OTHER INFORMATION: peptide epitope

<400> SEQUENCE: 3

Leu Val Phe Phe Ala Glu Asp Val
1               5

<210> SEQ ID NO 4
<211> LENGTH: 489
<212> TYPE: DNA
<213> ORGANISM: artificial sequence
<220> FEATURE:
<223> OTHER INFORMATION: monoclonal antibody 5E3, heavy chain, 3' read
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(21)
<223> OTHER INFORMATION: n is a, c, g, or t
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (44)..(47)
<223> OTHER INFORMATION: n is a, c, g, or t
<220> FEATURE:
<221> NAME/KEY: misc_feature
<222> LOCATION: (477)..(478)
<223> OTHER INFORMATION: n is a, c, g, or t
<220> FEATURE:
<221> NAME/KEY: misc_feature
<222> LOCATION: (483)..(489)
<223> OTHER INFORMATION: n is a, c, g, or t

<400> SEQUENCE: 4
nnnnnnnnnt nnnnnnnnnn nannnnnnnn annatagccc ttgnnnngca tcccagggtc      60
accatggagt tagtttgggc agcagatcca ggggccagtg gatagacaga tgggggtgtc     120
gttttggctg aggagactgt gagagtggtg ccttggcccc agtagtgagc ctcgtaatcc     180
atccttgcac agaaatagac cgcagagtcc tcagaggtca atctgctgag ctgcatgtag     240

```
gctgtgctgg aggatttgtc tgcagtcagt gtggccttgc ccttgaactt ctcattgtac      300
ttagtattaa catttccagg ataaatccat ccaatccact caagtccctg tccaggcctg      360
tgtatcaccc actgtatata gtagcttgtg aatatgtagc cagaagcctt gcaggatatc      420
ctcactgaag ccccaggctt caccagctca ggtccagact cctgcagctg cacctcnnaa      480 ttnnnnnnn                                                               489

<210> SEQ ID NO 5
<211> LENGTH: 486
<212> TYPE: DNA
<213> ORGANISM: artificial sequence
<220> FEATURE:
<223> OTHER INFORMATION: monoclonal antibody 5E3, heavy chain, 5' read
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (474)..(477)
<223> OTHER INFORMATION: n is a, c, g, or t
<220> FEATURE:
<221> NAME/KEY: misc_feature
<222> LOCATION: (484)..(486)
<223> OTHER INFORMATION: n is a, c, g, or t

<400> SEQUENCE: 5
nnnnnnnntg gngancctgg ggcttcngtg agganatcct gcaaggcttc tggctacata      60
ttcacaagct actatataca gtgggtgata cacaggcctg gacagggact tgagtggatt     120
ggatggattt atcctggaaa tgttaatact aagtacaatg agaagttcaa gggcaaggcc     180
acactgactg cagacaaatc ctccagcaca gcctacatgc agctcagcag attgacctct     240
gaggactctg cggtctattt ctgtgcaagg atggattacg aggctcacta ctggggccaa     300
ggcaccactc tcacagtctc ctcagccaaa acgacacccc catctgtcta tccactggcc     360
cctggatctg ctgcccaaac taactccatg gtgaccctgg gatgcctggt caagggctat     420
ttccctgagc cagtgacagt gacctggaac tctggatccc tgtccagcgg tgtnnnnaac    480 cttnnn                                                                486

<210> SEQ ID NO 6
<211> LENGTH: 373
<212> TYPE: DNA
<213> ORGANISM: artificial sequence
<220> FEATURE:
<223> OTHER INFORMATION: monoclonal antibody 5E3, light chain, 3' read
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
```

<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (356)..(357)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t

<400> SEQUENCE: 6
nnnnnnnnnn ngtttnattn nngcttggtg cctcctccga acgtccgagg ataattatga     60
tattgtagac agttgttgtc tgcacaatct tctcactcaa gggtgctgat ggggagagaa    120
taatctgaca cccacctact gccactgagc cttttttggga cacctcaatc ttgagtggat   180
gcggcgtaaa tcangcgttt aatagttccg tctggtttct gctgaagcca ggttaagtaa    240
ccactaattt cctgacttgc ccgacgagtg agactgactc tttctccctc agaggcagat    300
aangaggatg ganactgggt catctggatg tcacatctgg tacctggnaa ccngannnc     360 aaaaaancag caa                                                       373

<210> SEQ ID NO 7
<211> LENGTH: 374
<212> TYPE: DNA
<213> ORGANISM: artificial sequence
<220> FEATURE:
<223> OTHER INFORMATION: monoclonal antibody 5E3, light chain, 5' read
<220> FEATURE:
<221> NAME/KEY: misc_feature
<222> LOCATION: (1)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t

```
<400> SEQUENCE: 7
nnnnnnnnnn nnnnnnnncn ngtcnnntcc tccttatctg cctctctggg agaaaaagtc        60
cgtctcactt gtcgggcaag tcnagaaatt agtgcttact taacctggct tcagcagaga       120
ccccatggaa ctattagacg cccgatctaa cccccatcct ctttagattc tggtgtccca       180
aaaagggtcc ctgccaggat gtctgggtca gattattcta tcaacatcac catccttgag       240
tctgaagatt atgaagacga tgcctgtcta caatatggta attatcctcg gaagttcagt       300
ggaggcaacg agctagaaat ctaacaggct gatgctgcaa caactgtatc catcttccca       360
ccatcacacc atca                                                         374

<210> SEQ ID NO 8
<211> LENGTH: 7
<212> TYPE: PRT
<213> ORGANISM: artificial sequence
<220> FEATURE:
<223> OTHER INFORMATION: peptide epitope

<400> SEQUENCE: 8

Cys Gly Ser Asn Lys Gly Cys
1               5
```

OLIGOMER-SPECIFIC AMYLOID BETA EPITOPE AND ANTIBODIES

CROSS REFERENCE TO RELATED APPLICATIONS

This application is a Divisional of U.S. National Stage application Ser. No. 13/582,308, filed Aug. 31, 2012, which is the U.S. National Stage of International Application No. PCT/CA2011/000238, filed Mar. 3, 2011, which claims the benefit of U.S. Provisional Patent Application No. 61/310,167 filed Mar. 3, 2010, all of which are incorporated herein by reference in their entireties.

INCORPORATION OF SEQUENCE LISTING

The sequence listing that is contained in the file named "57964_151869_Seq_List.txt", which is 6,288 bytes (measured in operating system MS-Windows), created on Dec. 12, 2015, is filed herewith by electronic submission and incorporated herein by reference in its entirety. The sequence listing contains SEQ ID NOs: 1-8.

FIELD

The present invention relates to novel conformational epitopes in Abeta oligomers, related antibody compositions and methods of use.

BACKGROUND

Alzheimer's disease (AD) is a common dementing (disordered memory and cognition) neurodegenerative disease associated with brain accumulation of extracellular plaques composed predominantly of the Abeta (1-40), Aβ (1-42) and Aβ (1-43) peptides (also referred to as amyloid β or Aβ), all of which are proteolytic products of amyloid precursor protein (APP). In addition, neurofibrillary tangles, composed principally of abnormally phosphorylated tau protein (a neuronal microtubule-associated protein), accumulate intracellularly in dying neurons. The Aβ (1-42) is the dominant species in the amyloid plaques of AD patients.

Familial forms of AD can be caused by mutations in the APP gene, or in the presenilin 1 or 2 genes, the protein products of which are implicated in the processing of APP to Aβ. Apolipoprotein E allelic variants also influence the age at onset of both sporadic and familial forms of AD. More recently, it has been found that a particular molecular species of Aβ, in which the peptide is oligomerized, mediates the major component of neurotoxicity observed in AD and mouse models of the disease (Walsh et al. 2002). Aβ oligomer toxicity can be manifested by dysfunction of neuronal insulin receptors (Zhao et al. 2008), and by interference with normal synaptic function, particularly in the hippocampus, by ectopic activation of glutamatergic receptors (De Felice et al. 2007; Nimmrich et al. 2008). A nanomolar affinity binding interaction was reported between Aβ oligomers and the normal cellular isoform of the prion protein PrPC (Lauren et al. 2009). Further, interaction between PrPC and various toxic signaling pathways (Solforosi et al. 2004; Lefebvre-Roque et al. 2007), including glutamate receptor subunits (Khosravani et al. 2008), may lead to a unifying mechanism for the toxicity of Aβ oligomers.

It is well recognized that immune recognition of Aβ can lead to improvement in both the pathology and behavior of transgenic mice expressing human mutant amyloid precursor protein. However, there are dangers inherent in treating human beings with "non-selective" Aβ immunotherapies. For example, autoimmune meningoencephalitis occurred in approximately 10% of patients receiving an Alzheimer's vaccine containing a non-selective Aβ immunogen (Gelinas et al. 2004; Robinson et al. 2004; Broytman and Malter 2004; Mathews and Nixon 2003). Although the resulting meningoencephalitis was likely due to cellular immune activation to Aβ, it was also shown that passively infused Aβ monoclonal antibodies (mAbs), divorced from a cellular immune response, were associated with brain microhemorrhages (Goni and Sigurdsson 2005). Another risk of non-selective immunization with Aβ is immune recognition of the parent protein APP, which is exposed at the surface of brain neurons and circulating monocytes (Jung et al. 1996; Jung et al. 1990). Such recognition of a cell surface membrane molecule may trigger lysis or interference with functioning of the extracellular domain of the APP protein, which may include trophic activity (Morimoto et al. 1998; Mileusnic et al. 2005; Mileusnic et al. 2000).

Another problem with "non-specific" recognition of Aβ peptide is that Aβ peptide is only a precursor to the toxic Aβ molecular species, the Aβ oligomers. Aβ oligomers have been shown to kill cell lines and neurons in culture (Lambert et al. 2007; Lacor et al. 2007; Ronicke et al. 2008) and block a critical synaptic activity subserving memory, referred to as long term potentiation (LTP), in slice cultures and living animals (Balducci et al. 2010; Shenker et al. 2008; Selkoe 2008; Klyubin et al. 2005; Walsh et al. 2002; Wang et al. 2002). Specific Aβ oligomers have been identified which correlate to the onset of memory defects in mice, and which when purified and infused in normal young rats reproduces negative behavioral defects found in the mice (Lesne et al. 2000). Similar research has demonstrated that PrPC may serve as a receptor for Aβ oligomers, and may transduce its toxic effects in synaptic LTP disruption (Lauren et al. 2009).

Although Aβ vaccines and monoclonal antibodies have been raised in the past against Aβ peptides, none have to date been proven to produce the desired therapeutic effect without also causing serious side effects in animals and/or humans. There is a therapeutic need for the development of biologics that arrest or slow down the progression of the disease without inducing negative and potentially lethal effects on the human body. The need is particularly evident in view of the increasing longevity of the general population and, with this increase, an associated rise in the number of patents annually diagnosed with Alzheimer's disease. It would be desirable to identify immunological epitopes that are disease-specific epitopes (DSE) and develop immunotherapies that specifically target the toxic Aβ oligomeric molecular species. It is also desirable to develop immunotherapies to target toxic Aβ oligomeric molecular species and avoid autoimmune recognition of APP at the cell surface. Such DSE epitopes would be targets for immunotherapies and prophylactic vaccines, which specifically neutralize the toxicity of target proteins. It is also desirable to develop diagnostic tools to provide an indication of populations at risk for developing AD, for differential diagnosis to distinguish AD from other dementing syndromes, and for monitoring biomarker response to AD therapy.

It is therefore, desirable to provide a disease specific epitope that is unique to toxic Aβ oligomeric molecular species.

SUMMARY

It is an object of the present disclosure to obviate or mitigate at least one disadvantage of previous epitopes, antibodies, compositions and methods for diagnosis, treatment and prevention of Alzheimer's disease.

In a first aspect, the present disclosure is based, in part, on the surprising discovery of a novel structural epitope in AP with advantageous properties for selective antibody binding.

In one embodiment, there is provided a cyclic peptide derived from Aβ, having an amino acid the sequence of at least SNK corresponding to a solvent-exposed, antibody accessible "knuckle region" of oligomeric Aβ.

In another embodiment, there is provided an antigenic peptide comprising an epitope having a constrained cyclic configuration, the epitope having an amino acid sequence of at least SNK corresponding to a solvent-exposed, antibody accessible knuckle region of oligomeric Aβ.

In another embodiment, there is provided an antigenic peptide comprising an epitope having a constrained cyclic configuration, the epitope having an amino acid sequence corresponding to SEQ NO: 1 corresponding to a solvent-exposed, antibody accessible knuckle region of oligomeric Aβ.

In one aspect, the epitope of the antigenic peptide corresponds to residues 25 to 29 of oligomeric Aβ(1-40) or oligomeric Aβ (1-42).

In another embodiment, there is provided an isolated antibody that specifically binds to a cyclic peptide derived from Aβ, the cyclic peptide comprising a conformational epitope having an amino acid sequence of at least SNK corresponding to a solvent-exposed, antibody accessible knuckle region of oligomeric Aβ.

In another embodiment, there is provided an isolated antibody that specifically binds to a cyclic peptide derived from Aβ, the cyclic peptide comprising a conformational epitope having an amino acid sequence corresponding to SEC) ID NO: 1 corresponding to a solvent-exposed, antibody accessible knuckle region of oligomeric Aβ.

In one aspect, the isolated antibody specifically binds with greater affinity to an oligomeric form of Aβ than to a non-oligomeric form of Aβ.

In another aspect, the isolated antibody is monoclonal.

In another aspect, the isolated antibody is humanized.

In another embodiment, there is provided an immunoconjugate comprising an Isolated antibody that specifically binds to a cyclic peptide derived from Aβ, the cyclic peptide comprising a conformational epitope having an amino acid sequence of at least SNK corresponding to a solvent-exposed, antibody accessible knuckle region of oligomeric Aβ, conjugated with a detectable label.

In another aspect, them is provided a nucleic acid encoding the isolated antibody.

In another embodiment, them is provided a composition comprising a therapeutically effective amount of an isolated antibody that specifically binds to a cyclic peptide derived from Aβ, the cyclic peptide comprising a conformational epitope having an amino acid sequence of at least SNK corresponding to a solvent-exposed, antibody accessible knuckle region of oligomeric Aft and a pharmaceutically acceptable adjuvant.

In another embodiment, there is provided an anti-oligomeric vaccine composition comprising an antigenic peptide comprising an epitope having a constrained cyclic configuration, the epitope having an amino acid sequence of at least SNK corresponding to a solvent-exposed, antibody accessible knuckle region of oligomeric Aβ; and a pharmaceutically acceptable adjuvant.

In another aspect, there is provided a method of treating or preventing Alzheimer's Disease in a patient in need of said treatment comprising administering a pharmaceutically effective amount of the isolated antibody or immunconjugate.

In another aspect, there is provided a method of treating or preventing Alzheimer's Disease in a patient in need of said treatment comprising administering the vaccine.

In another aspect, there is provided a method of diagnosing Alzheimer's Disease in a patient suspected of having Alzheimer's Disease comprising the steps of: a) isolating a biological sample from the patient; b) contacting the biological sample with the isolated antibody for a time and under conditions sufficient to allow for formation of antigen/antibody complexes in the sample; and c) detecting the presence of the antigen/antibody complexes in the sample, wherein presence of the complexes indicates a diagnosis of Alzheimer's Disease in the patient.

In another embodiment, there is provided a kit for comprising: the isolated antibody and a conjugate comprising an antigen attached to a signal-generating compound.

In a further aspect, the kit comprises one or more detection agents.

In another embodiment, there is provided an article of manufacture comprising: the isolated antibody; a conjugate comprising an antigen attached to a signal-generating compound; and instructions for use in diagnosing Alzheimer's Disease.

In another aspect, there is provided use of the antibody or immunoconjugate for the treatment or prevention of Alzheimer's disease.

In another aspect, there is provided use of the vaccine for the treatment or prevention of Alzheimer's disease.

In another embodiment, there is provided isolated antibodies that are capable of binding to a cyclic peptide derived from Aβ and having an amino acid sequence of SNK corresponding to a solvent-exposed knuckle region of oligomeric Aβ. In one aspect, such antibodies bind oligomeric forms of Aβ with greater affinity than non-oligomeric forms of Aβ.

In another embodiment, there is provided a method of treatment of a subject having or suspected of having Alzheimer's disease, the method comprising administering to the subject a therapeutically effective amount of an antibody that is capable of binding to a cyclic peptide derived from Aβ having an amino acid composition comprising the sequence SNK. In one aspect, the antibody binds oligomeric forms of Aβ with greater affinity than non-oligomeric forms of Aβ.

In another embodiment, there is provided a method of preventing the development or progression of AD in a subject, the method comprising administering to the subject a therapeutically effective amount of an antigenic peptide comprising an epitope having a constrained cyclic configuration having an amino acid sequence of SNK corresponding to a knuckle region oligomeric Aβ. On administration, the antigenic peptide produces an Immune response against oligomeric Aβ. Antibodies produced are capable of specifically binding to oligomeric A. In certain embodiments, the antibody binds oligomeric forms of Aβ with greater affinity than non-oligomeric forms of Aβ.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 15 illustrates nucleotide sequences for the heavy and light chain, both 5' and 3' reads, of antibody 5E3.

DETAILED DESCRIPTION

Figure 1:
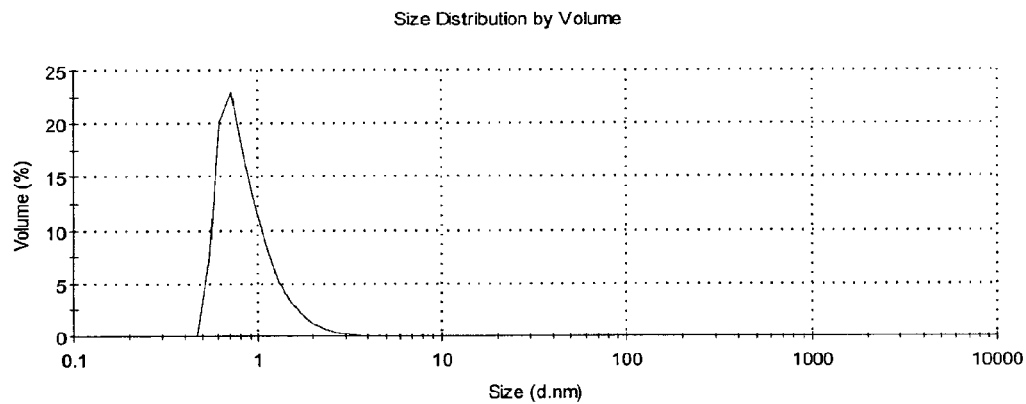
FIG. 1 graphically illustrates the results of dynamic light scattering which show the dynamic properties of monomeric Aβ.

Generally, the present disclosure provides a novel constrained peptide epitope derived from Aβ, from herein referred to as the "novel epitope" or "novel conformational epitope" and related antibody compositions. Antibodies capable of binding to the novel conformational epitope are useful as both diagnostics and therapeutic agents in the treatment of Alzheimer's disease. The novel constrained peptide epitope derived from Aβ is useful in vaccines for the prevention of AD and related dementias. Antibodies capable of binding to the novel conformational epitope are also useful in the diagnosis, treatment, and prevention of Alzheimer's related dementias.

Any terms not directly defined herein shall be understood to have the meanings commonly associated with them as understood within the art of the invention.

As used herein, the term "Isolated antibody" is used herein to refer to antibodies capable of binding to the novel conformational epitope, which are essentially pure and free from extraneous cellular material including other antibodies and antibody fragments having different antigenic specificities. An isolated antibody that specifically binds the novel conformational epitope may, however, have cross-reactivity to other antigens. A skilled person would readily appreciate that experimental conditions may have to be optimized for any given antibody to maximize specific binding. The term antibody is intended to include fragments thereof which also specifically react with the novel conformational epitope according to the invention. Antibodies can be fragmented using conventional techniques and the fragments screened for utility in the same manner as described above. For example, fragments can be generated by treating an antibody with pepsin. The resulting fragment can be further treated to reduce disulfide bridges.

As used herein, the term "subject" refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a mouse or a rat.

As used herein, the term "epitope" refers to a region within a molecule, which can be recognized by a specific antibody, or which induces the formation of specific antibodies.

As used herein, the term "conformational epitope" refers to an epitope where the amino acid sequence has a particular three-dimensional structure. Antibodies which specifically bind a conformation-specific epitope recognize the spatial arrangement of the amino acids of that conformation-specific epitope.

As used herein, the term 'Aβ' may alternately be referred to as 'amyloid beta', 'amyloid β', or 'Aβ'. Amyloid beta is a peptide of 39-43 amino acids that appears to be the main constituent of amyloid plaques in the brains of Alzheimer's disease patients. Aβ oligomerization has been shown to be a key part of neurotoxicity in Alzheimer's disease, as described elsewhere in this application.

As used herein, the term "greater affinity" herein refers to the degree of antibody binding where an antibody X binds to target Y more strongly and with a smaller dissociation constant than to target Z, and in this context antibody X has a greater affinity for target Y than for Z. Likewise, the term "lesser affinity" herein refers to a degree of antibody binding where an antibody X binds to target Y less strongly and with a larger dissociation constant than to target Z, and in this context antibody X has a lesser affinity for target Y than for Z.

As used herein, the term "Aβ monomer" herein refers to the isolated linear form of the Aβ (X-Y) peptide, preferably, a form of the Aβ (X-Y) peptide which is not engaged in essentially non-covalent interactions with other Aβ peptides.

As used herein, the term "Aβ ollgomer" herein refers to an isolated form of the Aβ peptide where the precursor Aβ monomer is non-covalently aggregated in an ordered three-dimensional structure of less than about 50 monomers.

As used herein, the term "Aβ fibril" herein refers to a molecular structure that comprises assemblies of non-covalently associated, individual Aβ(X-Y) peptides which show fibrillary structure under an electron microscope. The fibrillary structure is typically a "cross beta" structure; there is no theoretical upper limit on the size of multimers, and fibrils may comprise thousands of monomers.

As used herein, the term "antigen" herein refers to a molecule, such as a protein, polypeptide, or fragment thereof, containing one or more epitopes, that will stimulate a host's immune-system to make a humoral and/or cellular antigen-specific response. The term is used interchangeably with the term "immunogen." Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in DNA immunization applications, is also included in the definition of antigen herein.

Nomenclature used to describe the peptides of the present invention follows the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified.

In the description, for purposes of explanation, numerous details are set forth in order to provide a thorough understanding of the embodiments. However, it will be apparent to one skilled in the art that these specific details are not required.

The structure of Aβ oligomers at the atomic level has not been conclusively solved at the atomic level due to limitations of crystallography and NMR in solution and solid-state paradigms. Biochemical, biophysical and immunochemical data suggest a fibril/oligomer model in which Aβ monomers are packed in broad β hairpin steric zipper structures (Luhrs et al. 2005; Sawaya et al, 2007; Rauk 2009). The naturally occurring monomeric Aβ peptides undergo a conformation change upon aggregation involving folding and the formation of the hairpin steric zipper oligomeric Aβ structure results. Aβ(1-42) has a greater propensity for β-sheet aggregation. The detailed structure of oligomeric Aβ is unknown; however, structures of Aβ oligomers have been characterized using al combination of molecular dynamics simulation, atomic force microscopy, and amide hydrogen-exchange measurements. The structure of the Aβ(1-42) and Aβ(1-40) ollgomer has been analyzed using the above-noted methods. The orientation of the β strands of the Aβ oligomers is known by persons skilled in the art to include an intermolecular salt bridge between residues D23 and K28. In this configuration, the K28 residue is oriented substantially internally to form this salt bridge between D23 and K28 and stabilize the hairpin turn. (Lurs et al. 2005) and Rauk 2008).

An examination of proposed Aβ oligomer structures known in the art was conducted to identify regions against which an immune response may be specifically directed, and to which Aβ oligomer-specific antibodies may be developed. Inspection of the Aβ oligomer models illustrated three regions having solvent-exposed, potentially antibody-accessible residues available for binding: the Aβ oligomer N-terminus recognized by the mAb 6E10 (residues 4-9) of the Aβ peptide (FRHDSG identified as SEQ ID NO: 2); a mixed polar-hydrophobic domain in the N-terminal third of Aβ oligomer peptide (LVFFAEDV identified as SEQ ID NO. 3) recognized by the mAb 4G8 (residues 17-24); and a constrained turn domain of Aβ oligomer peptide comprised of the residues 25-29 (GSNKG). The discovery of the constrained turn domain epitope comprising SNK residues 26-28 is conformationally constrained and would not be present on linear Aβ or APP. Antibodies directed against this conformationally constrained epitope would not be expected bind linear Aβ or APP, and would be Aβ oligomer-specific antibodies.

Figure 4:
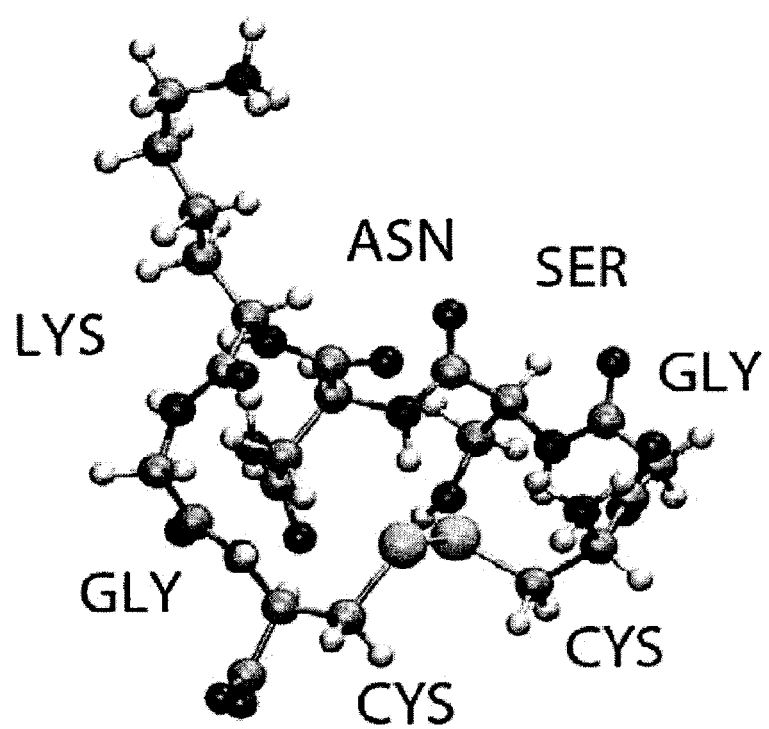
FIG. 4 is a three-dimensional model of the disulfide-cyclized peptide comprising the SNK epitope.

Image capture of molecular dynamics modeling of a disulfide-linked cyclic peptide comprising residues 25-29 (CGSNKGC) (SEQ ID NO: 8) was conducted; non-native cysteines were added for disulfide linkage. This modeling reveals that the side chain of lysine 28 is oriented externally as shown in FIG. 4, in contrast to the internally oriented lysine 28 side chain predicted in reference Lurs et al. (2005) and Rauk (2008). The surprising discovery of the outward orientation of the lysine 28 residue is consistent with the high immunogenicity of this cyclic peptide comprising residues 25-29 (CGSNKGC) (SEQ ID NO:8), the side of lysine being solvent exposed, large and charged via an ε-amino group. Antibodies directed to a conformational cycle epitope comprising at least the SNK residues have been shown in the examples below to effectively neutralize the toxicity of Aβ oligomers, see for example FIG. 11. The surprising discovery of the outward orientation of the lysine 28 residue is also consistent with authentic Aβ oligomers also displaying a similar lysine sidechain orientation into solvent in an antibody-accessible fashion. The serine 26, asparagine 27 and lysine 28 residues, SNK, located in the knuckle region of Aβ oligomers are all charged or polar, and have greater immunogenicity than small non-polar amino acids. The cyclic conformation of the SNK residues, located in the knuckle region of Aβ oligomers, form a novel conformational epitope that is solvent exposed and available for antibody binding. The following examples described below confirm the discovery of the availability of the conformationally constrained SNK epitope of Aβ oligomers for binding. The discovery of this novel structurally constrained epitope at the surface of Aβ oligomers has advantageous properties for selective antibody binding.

The novel conformational epitope may further include a native glycine located at either end of the SNK epitope sequence. The novel conformational epitope may further include native glycine residues at both ends of the epitope sequence. In one aspect, the native glycine residues have limited or no contribution to the immunogenicity of the novel conformational epitope however, the glycine residues may relieve some steric tension inherent in the cyclization of the peptide. In the amino acid structure formulae, each residue may be generally represented by a one-letter or three-letter designation, corresponding to the trivial name of the amino acid. In accordance with the following Table 1.

TABLE 1

Nomenclature and abbreviations of the 20 standard L-amino acids commonly found in naturally occurring peptides.

| Full Amino Acid name | Three-letter abbreviation | One-letter abbreviation |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |

TABLE 1-continued

Nomenclature and abbreviations of the 20 standard L-amino acids commonly found in naturally occurring peptides.

| Full Amino Acid name | Three-letter abbreviation | One-letter abbreviation |
| --- | --- | --- |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

The epitope is comprised of strongly polar/charged residues that are solvent-exposed and structurally constrained at the surface of Aβ oligomers. The epitope is comprised of at least residues 26-28, SNK, in a cyclic constrained configuration. In another aspect, the epitope is comprised of residues 25-28, GSNK, in a cyclic constrained configuration. In a further aspect, the epitope is comprised of residue 20-29, SNKG, in a cyclic constrained configuration. In another aspect, the epitope is comprising of residues 25-29, GSNKG (SEQ ID NO:1) in a cyclic constrained configuration.

In one aspect, the structure of the novel conformation-specific epitope is dependent on a relatively-rigid spatial arrangement of the amino acid residues.

In contrast to the known epitopes identified as SEQ ID NO: 2 and SEQ ID NO: 3, which bind known antibodies 0E10 and 4G8 respectively, that are expressed on the solvent-exposed surface of Aβ oligomers and at the surface of cells supporting the expression of the parent protein APP (both neurons and monocytes), the novel conformational epitope having a constrained cyclic configuration is not present on the molecular surface of APP thus limiting the autoimmune recognition of APP. The GSNKG motif of APP that is located at the cell surface of neurons and monocytes is largely unstructured. Conformation-specific antibodies binding to the novel conformational epitope having a constrained cyclic configuration have limited or no recognition of the unstructured GSNKG motif on cell surface APP as is shown in the Examples below. Antibodies recognizing the novel conformational epitope show little or no reaction with monomeric Aβ. In another aspect, antibodies recognizing the novel conformational epitope show little or no reaction with fibril Aβ, due to steric crowding of the epitope and/or other unfavourable aspects.

Antibodies to the novel conformational epitope are provided in another aspect of the present disclosure. Analysis indicates that antibodies binding to the to the novel conformational epitope having a constrained cyclic configuration recognize the non-linear epitope structure in between the subunits in the region of amino acids 25-29 of Aβ oligomers. The specificity of the antibodies to the novel conformational epitope enables the antibodies to specifically target the oligomeric form of Aβ and as such, avoid targeting monomeric Aβ and APP that are known to impact on neuronal and immune function and increase the availability of the antibody for binding as monomeric Aβ is present in much larger quantities than oligomeric A.

Antibodies capable of binding to the novel conformational epitope are useful as both diagnostics, therapeutic agents in the treatment of Alzheimer's disease, and vaccines for the prevention of AO are provided in another aspect of the present invention.

Antibodies that specifically bind to the cyclic peptide, comprising novel conformational epitope, derived from Aβ as described herein include antibodies synthesized from the disulfide cyclic peptide comprising the novel conformational epitope.

For use as a therapeutic, an antibody that specifically binds a cyclic peptide derived from Aβ, where the cyclic peptide comprises an conformational epitope having an amino acid sequence of at least SNK corresponding to a knuckle region of oligomeric Aβ, may be made using standard, well-established methods of antibody manufacturing. A therapeutic composition comprises an antibody that specifically binds a cyclic peptide derived from Aβ, where the cyclic peptide comprises an epitope having an amino acid sequence of at least SNK corresponding to a knuckle region of oligomeric Aβ in combination with a pharmaceutically acceptable adjuvant. Such a therapeutic may be administered to a patient in need of treating or preventing Alzheimer's disease. In one aspect, such a therapeutic may delay the onset of Alzheimer's disease.

The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with peptide-based drugs, such as diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously, intramuscularly or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, anti-oxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations, for example, for nasal delivery, may also be prepared in which suitable propellant adjuvants are used. Other adjuvants may also be added to the composition regardless of how it is to be administered, for example, anti-microbial agents may be added to the composition to prevent microbial growth over prolonged storage periods. Therapeutic compositions typically must be sterile and stable under conditions of manufacture and storage.

For use as a vaccine, an antigenic peptide comprising a conformationally constrained epitope having an amino acid sequence of at least SNK corresponding to a knuckle region of oligomeric Aβ in combination with a pharmaceutically acceptable adjuvant, when administered generates antibodies that specifically target the oligomeric Aβ. These antibodies that specifically bind an epitope having an amino acid sequence of at least SNK corresponding to a knuckle region of oligomeric Aβ. A vaccine comprises an antigenic peptide comprising a conformationally constrained epitope having an amino acid sequence of at least SNK corresponding to a knuckle region of oligomeric Aβ in combination with a pharmaceutically acceptable adjuvant. The vaccine blocks the development of brain amyloidosis through neutralizing the oligomeric Aβ and acts to prevent the development of AO. Where oligomeric Aβ is blocked, their associated toxicity is blocked. Such toxicity may include for example, synaptic dysfunction and neuronal cell death. In another aspect, the antibodies generated on administration of a vaccine described above delays the propagation of oligomeric Aβ, as such the antibodies delay the monomer Aβ aggregation into the toxic oligomer Aβ form. In a further aspect, the antibodies generated on administration of a vaccine described above block the propagation of oligomeric Aβ, as such the antibodies block the monomer Aβ aggregation into the toxic oligomer Aβ form.

Examples of pharmaceutically acceptable adjuvants may include aluminum hydroxide, alum, Alhydrogel™ (aluminum trihydrate) or other aluminum-comprising salts, virosomes, nucleic acids comprising CpG motifs, squalene, oils, MF59, QS21, various saponins, virus-like particles, monophosphoryl-lipidA/trehalose dicorynomycolate, toll-like receptor agonists, copolymers such as polyoxypropylene and polyoxyethylene, or the like.

The vaccine may be administered to a patient population at risk for developing Alzheimer's disease, for example an advanced age population, a known population of "at risk" individuals harboring a known AD-promoting mutation.

In one embodiment, for treatment with a vaccine, subjects are immunized on a schedule that can vary from once a day, to once a week, to once a month, to once a year, to once a decade. A typical regimen includes an immunization followed by booster injections at 6 weekly intervals. Another regimen consists of immunization followed by booster injections 1, 2 and 12 months later. Alternatively, booster injections will vary depending on the immune response and the physiological condition of the subject. For immunization, the anti-oligomeric vaccine can be administered in a dose that ranges from about 0.0001 microgram to 10 grams, about 0.01 microgram to about 1 gram, about 1 microgram to about 1 mg, and about 100 to 250 micrograms per treatment. In one embodiment the timing of administering treatment is at one or more of the following: 0 months, 2 months, 6 months, 9 months, and/or 12 months. In one regimen, the dosing is at 2, 6, 9, and 12 months following the first immunization. In another regimen, the dosing is at 2 and 4 weeks following the first immunization, and then monthly afterwards. In an alternative regimen, the dosing varies depending on the physiological condition of the subject and/or the response to the subject to prior immunizations. The route of administration optionally includes, but is not limited to, intramuscular and intraperitoneal injections. In one embodiment the composition is injected into the deltoid muscle.

For use as a diagnostic or treatment-responsive biomarker, a suitable biological sample is isolated from a patient; the sample is contacted with an antibody that specifically bind a cyclic peptide derived from Aβ, where the cyclic peptide comprises an epitope having an amino acid sequence of at least SNK corresponding to a knuckle region of oligomeric Aβ for a period of time under conditions that are suitable to allow for the formation of antigen/antibody complexes; and the presence of the complexes is detected. Where complexes are detected there is an indication of a diagnosis of AD in the patient. A suitable biological sample for this purpose includes tissues, cells, and biofluids including for example cerebrospinal fluid (CSF) and blood.

In use, antibodies that bind the novel conformational epitope are of great diagnostic value in AD. To assist with the identification of subjects who are candidates for treatment with the antibody or vaccine compositions of the invention, the present invention further provides for the detection of an epitope by in vitro or in vivo diagnostic methods.

To detect the presence of oligomeric Aβ in any given sample, the present invention provides a detection method in which a sample suspected to contain oligomeric Aβ is treated with an antibody or binding fragment that binds selectively to the novel conformational epitope presented uniquely by the oligomeric Aβ relative to monomeric Aβ and APP; and determining whether an antigen:antibody complex has formed, the formation thereof being indicative of the presence in the sample of a oligomeric Aβ. The presence of the antigen:antibody complexes further indicates a diagnosis of AD in the patient.

When applied in vitro, the detection method entails analysis of a biological sample of body fluid or tissue or organ sample from a subject, usually a subject suspected of having AD. A tissue or organ sample, such as that obtained from a solid or semi-solid tissue or organ, may be digested, extracted or otherwise rendered to a liquid form. A biological sample or samples may be taken from a subject at any appropriate time, including before the subject is diagnosed with, or suspected of having AD or a related dementia, during a therapeutic regimen for the treatment or amelioration of symptoms of that disease or disorder, after death of the subject (regardless of the cause, or suspected cause). Alternately, a biological sample may include donated body fluid or tissue, such as blood, plasma or platelets when in care of a centralized blood supply organization or institution.

The presence of oligomeric Aβ in the sample is confirmed if the antibody forms a detectable antigen:antibody complex. The formation of such complex can be determined using a wide variety of protocols that include ELISA, RIA, flow cytometry, Western blots, immunohistochemistry and the like. To reveal the complex and hence the presence of the novel conformational epitope in the sample, the antibody desirably is provided as a labeled antibody by conjugation or coupling to an agent that is detectable either visually or with the aid of instrumentation. The agent, or label, is capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. Alternatively, the novel conformational epitope can be revealed using a labeled secondary reagent that binds to the epitope antibody, such as a labeled antibody that binds the epitope antibody, to reveal presence of the epitope indirectly. The presence of an antibody:antigen complex may be detected by indirect means that do not require the two agents to be in solution. For instance, the complex is detectable indirectly using flow cytometry, where the antibody binds to, and forms an antibody:antigen complex with, the epitope presented on the surface of an intact cell. It will also be appreciated that the antigen:antibody complex can also be identified by non-antibody based methods, that include those which sort proteins based on size, charge and mobility, such as electrophoresis, chromatography, mass spectroscopy and the like.

In a related embodiment, the labeled antibodies of the invention, or labeled form of a binding fragment thereof, can be used in vivo to image the presence of the oligomeric Aβ to which the antibody binds. To this end, the present invention provides an antibody or fragment in a form coupled to an agent useful for in vivo imaging, such as isotopes of technetium, gadolinium, and the like.

In another aspect, an article of manufacture (also referred to as a commercial package) is provided comprising packaging material and a pharmaceutical composition. The composition comprises a pharmaceutically acceptable adjuvant and a therapeutically effective amount of a conformationally-sensitive antibody that specifically binds a cyclic peptide derived from Aβ, where the cyclic peptide comprises an epitope having an amino acid sequence of at least SNK corresponding to a knuckle region of oligomeric Aβ. The packaging material may be labelled to indicate that the composition is useful to treat Alzheimer's disease. The packaging material may be any suitable material generally used to package pharmaceutical agents including, for example, glass, plastic, foil and cardboard.

In another aspect, an article of manufacture is provided comprising packaging material and a pharmaceutical composition. The composition comprising a peptide comprising a conformationally constrained epitope having an amino acid sequence of at least SNK corresponding to a knuckle region of oligomeric Aβ in combination with a pharmaceutically acceptable adjuvant, as provided herein. The composition may include a physiologically or pharmaceutically acceptable excipient, and the packaging material may include a label which indicates the active ingredients of the composition (e.g. the peptide). The label may further include an intended use of the composition, for example as a therapeutic or prophylactic reagent, or as a composition to induce an immune response in a subject for the purpose of producing antisera or antibodies specific to oligomeric Aβ, to be used with kits as set out herein.

In a further embodiment, there is provided a kit comprising a composition comprising a peptide as provided herein, along with instructions for use of the compound or composition for the production or screening of conformationally-sensitive antibodies for identification of oligomeric Aβ. The kit may be useful for production and/or identification of oligomeric Aβ specific antibodies or antisera, and the instructions may include, for example, dose concentrations, dose intervals, preferred administration methods, methods for immunological screening or testing, or the like.

In another embodiment, a kit for the preparation of a medicament, comprising a composition comprising one or more peptides as provided herein, along with instructions for its use is provided. The instructions may comprise a series of steps for the preparation of the medicament, the medicament being useful for inducing a therapeutic or prophylactic immune response in a subject to whom it is administered. The kit may further comprise instructions for use of the medicament in treatment, for treatment, prevention or amelioration of one or more symptoms of AD or related dementias, and include, for example, dose concentrations, dose intervals, preferred administration methods or the like.

In another embodiment, a kit for diagnosing a AD or related dementias is provided. The kit comprises one or more conformationally-sensitive and selective antibodies or antisera as described herein, along with instructions for its use. The antibody may further be coupled to a detection reagent. Examples of detection reagents include secondary antibodies, such as an anti-mouse antibody, an anti-rabbit antibody or the like. Such secondary antibodies may be coupled with an enzyme that, when provided with a suitable substrate, provides a detectable calorimetric or chemiluminescent reaction. The kit may further comprise reagents for performing the detection reaction, including enzymes such as proteinase K, blocking buffers, homogenization buffers, extraction buffers, dilution buffers or the like.

In another embodiment, a kit for detecting the presence of oligomeric Aβ in a biological sample is provided. The kit comprises one or more conformationally-sensitive antibodies or antisera that specifically bind the oligomeric Aβ, along with instructions for its use. The antibody may further be coupled to a detection reagent. Examples of detection reagents include secondary antibodies, such as an anti-mouse antibody, an anti-rabbit antibody or the like. Such secondary antibodies may be coupled with an enzyme that, when provided with a suitable substrate, provides a detectable calorimetric or chemiluminescent reaction. The kit may further comprise reagents for performing the detection reaction, including enzymes such as proteinase K, blocking buffers, homogenization buffers, extraction buffers, dilution buffers or the like.

Conventional methods can be used to prepare the conformationally-sensitive antibodies including polyclonal antisera or monoclonal antibodies. To produce polyclonal antibodies, a mammal, (e.g. a mouse, hamster, or rabbit) can be immunized with an immunogenic form of the novel conformational epitope which elicits an antibody response in the mammal. For example, a disulfide-linked cyclized peptide comprising the novel conformational epitope sequence may be constrained in a loop conformation using a disulfide linkage between cysteines at the N- and C-termini of this peptide. The disulfide-linked cyclized peptide may be synthesized using conventional techniques and introduced into a mammal.

Techniques for conferring immunogenicity on a peptide are well known in the art and include, for example, conjugation to carriers. The peptide can be administered in the presence of adjuvant. The progress of immunization can be monitored by detection of antibody titers in plasma or serum. Standard ELISA or other immunoassay procedures can be used with the immunogen as antigen to assess antibody levels. Following immunization, antisera can be obtained and, if desired, polyclonal antibodies isolated from the sera.

To produce monoclonal antibodies, antibody-producing cells (B-lymphocytes) are harvested from an immunized animal and fused with myeloma cells by standard somatic cell fusion procedures to form immortal hybridoma cells. Such techniques are well known in the art, (e.g., the hybridoma technique originally developed by Kohler and Milstein (Nature 256, 495-497(1975)) as well as other techniques such as the human B-cell hybridoma technique (Kozbor et al., Immunol. Today 4, 72 (1983)), the EBV-hybridoma technique to produce human monoclonal antibodies (Cole et al., Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with a selected novel conformational epitope and the monoclonal antibodies can be isolated.

A typical antibody is composed of two immunoglobulin (Ig) "heavy chains" and two Ig "light chains" and may be thought of as adopting a general Y-shaped configuration. Several different types of heavy chain exist that define the class or isotype of an antibody. There are five types of mammalian immunoglobulin heavy chain: γ, δ, α, μ and ε, and these define classes of immunoglobulins: IgG, IgD, IgA, IgM and IgE, respectively. There are two types of light chain in mammals: kappa (κ) chain, and lambda (λ) chain.

Each heavy chain has two regions: a constant region, which is the same for all immunoglobulins of the same class but differs between classes (heavy chains γ, α and δ have a constant region composed of three tandem immunoglobulin domains (CH1, CH2, CH3) but also have a hinge region for added flexibility; heavy chains μ and ε have a constant region composed of four domains); and a variable region (VH) that differs between different B cells, but is the same for all immunoglobulins produced by the same B cell or B cell clone. The variable domain of any heavy chain is composed of a single immunoglobulin domain. These domains are about 110 amino acids long.

Each light chain is composed of two tandem immunoglobulin domains: one constant (CL) domain; and one variable domain (VL) that is important for binding antigen.

Some parts of an antibody have unique functions. The arms of the "Y", for example, contain the sites that can bind two antigens (in general identical) and, therefore, recognize specific foreign objects. This region of the antibody is called the "Fab" (fragment, antigen binding) region. It is composed of one constant and one variable domain from each heavy and light chain of the antibody. The "paratope" is shaped at the amino terminal end of the antibody monomer by the variable domains from the heavy and light chains. The variable domain is also referred to as the FV region and is the most important region for binding to antigens. More specifically, variable loops of β-strands, three each on the light (VL) and heavy (VH) chains are responsible for binding to the antigen. These loops are referred to as the complementarity determining regions ("CDRs").

Complementarity determining regions ("CDRs") are regions within antibodies where these proteins complement an antigen's shape. Thus, CDRs determine the protein's affinity and specificity for specific antigens. The CDRs are the most variable part of the molecule, and contribute to the diversity of these molecules, allowing the antibody to recognize a vast repertoire of antigens.

In the amino acid sequence of a variable domain of an antigen receptor there are three CDRs (CDR1, CDR2 and CDR3), arranged non-consecutively. Since the antigen receptors are typically composed of two variable domains (on two different polypeptide chains, heavy and light chain), there are six CDRs for each antigen receptor that can collectively come into contact with the antigen. A single antibody molecule has two antigen receptors, therefore it contains twelve CDRs.

The base of the general "Y" shape of an antibody plays a role in modulating immune cell activity. This region is called the Fc (Fragment, crystallizable) region, and is composed of two heavy chains that contribute two or three constant domains depending on the class of the antibody. The Fc region ensures that each antibody generates an appropriate immune response for a given antigen, by binding to a specific class of Fc receptors, and other immune molecules, such as complement proteins. By doing this, it mediates different physiological effects including recognition of opsonized particles, lysis of cells, or degranulation of mast cells, basophils or eosinophils.

There are number of ways to designated CDRs in an amino acid sequence. The "Kabat" definition is based on sequence variability and is most commonly used. The "Chothia" definition is based on location of structural loop regions. The "AbM" definition is a compromise between the two used by Oxford Molecular's AbM antibody modelling software. The "contact" definition is based on an analysis of available complex crystal structures.

A skilled person could readily identify CDR's in any given sequence comprising CDR's, using known patterns and sequence alignment methods. In another aspect, modeling or other methods known to the skilled person may also be used for CDR identification. There are well known guidelines, for example those set out in the following website (http://www.bioinf.org.uk/abs/), in the art to assist the skilled person in identifying the CDRs in an antibody sequence.

The heavy and light chains of the 5E3 antibody were sequenced. The heavy chain sequence and light chain sequence corresponds to the sequences identified in FIG. 15. A skilled person would appreciate that portions of the above sequence which are determinants of antigen binding could be transferred to another antibody framework, for example, to generate a "chimeric" or "humanized" antibody.

A skilled person could readily align the 5' and 3' sequence reads illustrated in FIG. 15 to generate a consensus sequence (for example, using available software packages such as GCG or Sequencher), and could examine sequence traces where required to resolve discrepancies. Any remaining discrepancies could be resolved by resequencing. Discrepancies, for example, a middle stop codon located in a nucleotide sequence would be known to a person skilled in the art as an obvious nucleotide misread. It is well known in the art that when sequences amino acids and nucleotides that sequencing errors or miscalls may occur when a sequencing method calls one or more bases incorrectly, leading to an inaccurate read. Due to the vagaries of molecular biology, no laboratory-based DNA sequencing methods are perfectly precise; they are all known to miscall bases occasionally in the machines. Such miscalls become evident when the sequence read is aligned against other reads or against a reference.

"Chimeric" antibodies are also contemplated within the scope of the invention. Chimeric antibodies may comprise sequences from two different antibodies. They may comprise sequences from antibodies from two different species. Chimeric antibody molecules can include, for example, the antigen binding domain from an antibody of a mouse, rat, or other species with a constant human peptide region. Conventional methods may be used to make chimeric antibodies containing the immunoglobulin variable region which recognizes the novel conformational epitope of the invention (See, for example, Morrison et al., Proc. Natl Acad. Sci, U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

"Humanized antibodies" comprise antibody sequences from non-human species whose protein sequences have been modified to increase their similarity to antibody variants produced naturally in humans. These may be considered as a specific subset of chimeric antibodies, in some instances.

However, "humanization" is usually seen as distinct from the creation of a simple chimera. Having said that, the humanization process may include the creation of a mouse-human chimera in an initial step (for example, a mouse Fab may be spliced to human Fc). Thereafter the chimera might be further humanized by the selective alteration of the sequence of amino acids in the Fab portion of the molecule. The process is usually "selective" to retain the specificity for which the antibody was originally developed. For example, aside from the CDR segments, the portions of the Fab sequence that differ from those in humans can be mutated by exchanging the appropriate individual amino acids. This is accomplished at the DNA level using mutagenesis. It is possible to produce a humanized antibody without creating a chimeric intermediate. "Direct" creation of a humanized antibody can be accomplished by inserting the appropriate CDR coding segments (responsible for the desired binding properties) into a human antibody "scaffold". As discussed above, this is achieved through recombinant DNA methods using an appropriate vector and expression in mammalian cells. That is, after an antibody is developed in mouse (for example) which exhibits the desired properties, the DNA coding for that antibody can be isolated, cloned into a vector and sequenced. The DNA sequence corresponding to the antibody CDRs can then be determined. Once the precise sequence of the desired CDRs are known, a strategy can be devised for inserting these sequences appropriately into a construct containing the DNA for a human antibody variant. The strategy may also employ synthesis of linear DNA fragments based on the reading of CDR sequences. Diversity libraries may be generated using synthetic diversity-containing oligonucleotide primers. The resulting pool of clones may be further screened to identify optimized humanized antibody clones using known methods.

In some embodiments, monoclonal or chimeric antibodies specifically reactive with the novel conformational epitope of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al, Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great. Britain).

In one aspect, there is provided a chimeric or humanized antibody comprising the heavy and/or light chains sequences of 5E3, or a portion or portions thereof. The portions may be the determinants of antigen binding. In some embodiments, determinants may comprise the CDR sequences of 5E3. Such antibodies bind the same epitope as 5E3. They may also bind an epitope which at least partially overlaps that bound by 5E3.

In some embodiments, the chimeric or humanized antibody may comprise CDR sequences substantially identical to the CDR sequences of 5E3. In some embodiments, the antibody may have conservative sequence changes compared to the sequences of 5E3.

Among the common amino acids a "conservative amino acid substitution" is exemplified by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table, which is well-known in the art, is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

In some embodiments, the antibody may comprise CDR sequences which are at least 70%, at least 75%, at least 80%, at least 85% or at least 90% identical to the CDR sequences of 5E3. They may also be at least 91%, at least 92%, at least 93%, at least 94%, at least 95%, at least 96%, at least 97%, at least 98%, at least 99% or greater than 99% identical to the CDR sequences of 5E3.

Standard recombinant DNA and molecular cloning techniques used in the making of antibodies are well known in the art and are described more fully in Sambrook, J., Fritsch, E. F. and Maniatis, T., Molecular Cloning: A Laboratory Manual; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of Isolated segments of nucleic acids by genetic engineering techniques.

The dosage of the compositions or compounds of some embodiments of the Invention may vary depending on the route of administration (oral, Intravenous, inhalation, or the like) and the form in which the composition or compound is administered (solution, controlled release or the like). Determination of appropriate dosages is within the ability of one of skill in the art.

A "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The pharmaceutical compositions of the invention may include an "effective amount", "therapeutically effective amount" or a "prophylactically effective amount" of an antibody or antibody portion of the invention A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount. The effective amount may be calculated on a mass/mass basis (e.g. micrograms or milligrams per kilogram of subject), or may be calculated on a mass/volume basis (e.g. concentration, micrograms or milligrams per milliliter). Using a mass/volume unit, an antibody may be present at an amount from about 0.1 µg/ml to about 20 mg/ml, or any amount therebetween, for example 0.1, 0.5, 1, 2, 5, 10, 15, 20, 25, 30, 35, 40, 50, 60, 70, 80, 90, 100, 120, 140, 160 180, 200, 250, 500, 750, 1000, 1500, 2000, 5000, 10000, 20000 µg/ml, or any amount therebetween; or from about 1 µg/ml to about 2000 µg/ml, or any amount therebetween, for example 1.0, 2.0, 5.0, 10.0, 15.0, 20.0, 25.0, 30.0, 35.0, 40.0, 50.0 60.0, 70.0, 80.0, 90.0, 100, 120, 140, 160 180, 200, 250, 500, 750, 1000, 1500, 2000, µg/ml or any amount therebetween; or from about 10 ug/ml to about 1000 ug/ml or any amount therebetween, for example 10.0, 15.0, 20.0, 25.0, 30.0, 35.0, 40.0, 50.0 60.0, 70.0, 80.0, 90.0, 100, 120, 140, 160 180, 200, 250, 500, 750, 1000 µg/ml, or any amount therebetween; or from about 30 ug/ml to about 1000 ug/ml or any amount therebetween, for example 30.0, 35.0, 40.0, 50.0 60.0, 70.0, 80.0, 90.0, 100, 120, 140, 160 180, 200, 250, 500, 750, 1000 µg/ml.

Quantities and/or concentrations may be calculated on a mass/mass basis (e.g. micrograms or milligrams per kilogram of subject), or may be calculated on a mass/volume basis (e.g. concentration, micrograms or milligrams per milliliter). Using a mass/volume unit, an antibody or peptide may be present at an amount from about 0.1 µg/ml to about 20 mg/ml, or any amount therebetween, for example 0.1, 0.5, 1, 2, 5, 10, 15, 20, 25, 30, 35, 40, 50, 60, 70, 80, 90, 100, 120, 140, 160 180, 200, 250, 500, 750, 1000, 1500, 2000, 5000, 10000, 20000 µg/ml, or any amount therebetween; or from about 1 µg/ml to about 2000 µg/ml, or any amount therebetween, for example 1.0, 2.0, 5.0, 10.0, 15.0, 20.0, 25.0, 30.0, 35.0, 40.0, 50.0 60.0, 70.0, 80.0, 90.0, 100, 120, 140, 160 180, 200, 250, 500, 750, 1000, 1500, 2000, µg/ml or any amount therebetween; or from about 10 ug/ml to about 1000 ug/ml or any amount therebetween, for example 10.0, 15.0, 20.0, 25.0, 30.0, 35.0, 40.0, 50.0 60.0, 70.0, 80.0, 90.0, 100, 120, 140, 160 180, 200, 250, 500, 750, 1000 µg/ml, or any amount therebetween; or from about 30 ug/ml to about 1000 ug/ml or any amount therebetween, for example 30.0, 35.0, 40.0, 50.0 60.0, 70.0, 80.0, 90.0, 100, 120, 140, 160 180, 200, 250, 500, 750, 1000 µg/ml.

The antibodies of the invention may be incorporated into a pharmaceutical composition suitable for, for example, parenteral administration. Preferably, the antibody or will be prepared as an injectable solution containing an effective amount of antibody. The injectable solution can be composed of either a liquid or lyophilized dosage form in a flint or amber vial, ampule or pre-filled syringe. Any suitable buffer may be used in the preparation of the pharmaceutical compositions. Examples of such buffers include but are not limited to, sodium succinate, sodium citrate, sodium phosphate or potassium phosphate. Cryoprotectants and bulking agents may be included for a lyophilized dosage form. Stabilizers may be used in both liquid and lyophilized dosage forms.

Compositions according to various embodiments of the invention, including therapeutic compositions, may be administered as a dose comprising an effective amount of an antibody or peptide. The dose may comprise from about 0.1 µg/kg to about 20 mg/kg (based on the mass of the subject), for example 0.1, 0.5, 1, 2, 5, 10, 15, 20, 25, 30, 35, 40, 50, 60, 70, 80, 90, 100, 120, 140, 160 180, 200, 250, 500, 750, 1000, 1500, 2000, 5000, 10000, 20000 µg/kg, or any amount therebetween; or from about 1 µg/kg to about 2000 ug/kg or any amount therebetween, for example 1.0, 2.0, 5.0, 10.0, 15.0, 20.0, 25.0, 30.0, 35.0, 40.0, 50.0 60.0, 70.0, 80.0, 90.0, 100, 120, 140, 160 180, 200, 250, 500, 750, 1000, 1500, 2000 µg/kg, or any amount therebetween; or from about 10 ug/kg to about 1000 ug/kg or any amount therebetween, for example 10.0, 15.0, 20.0, 25.0, 30.0, 35.0, 40.0, 50.0 60.0, 70.0, 80.0, 90.0, 100, 120, 140, 160 180, 200, 250, 500, 750, 1000 µg/kg, or any amount therebetween; or from about 30 ug/kg to about 1000 ug/kg or any amount therebetween, for example 30.0, 35.0, 40.0, 50.0 60.0, 70.0, 80.0, 90.0, 100, 120, 140, 160 180, 200, 250, 500, 750, 1000 µg/kg.

One of skill in the art will be readily able to interconvert the units as necessary, given the mass of the subject, the concentration of the pharmaceutical composition, individual components or combinations thereof, or volume of the pharmaceutical composition, individual components or combinations thereof, into a format suitable for the desired application.

The pharmaceutical compositions of the present invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The antibodies of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, Including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with a material to prevent its inactivation.

Supplementary active compounds may also be incorporated into the pharmaceutical compositions. In certain embodiments, an antibody of the invention is co-formulated with and/or co-administered with one or more additional therapeutic agents that are useful for treating AD or related dementias. For example, one of the antibodies of the subject invention or antibody portion thereof may be co-formulated and/or co-administered with one or more additional antibodies that bind other targets.

In certain embodiments, an antibody of the present invention or fragment thereof may be linked to a half-life extending vehicle known in the art. Such vehicles include, but are not limited to, the Fc domain, polyethylene glycol (PEG), and dextran. Such vehicles are described, e.g., in U.S. application Ser. No. 09/428,082 and published PCT Application No. WO 99/25044, which are hereby incorporated by reference for any purpose.

In one embodiment of the invention, there is provided an antigenic peptide comprising an epitope having a constrained cyclic configuration, the epitope comprising an amino acid sequence of at least SNK, the epitope corresponding to a solvent exposed, antibody accessible knuckle region of oligomeric Aβ.

In another embodiment of the invention, there is provided an antigenic peptide comprising an epitope having a constrained cyclic configuration, the epitope having an amino acid sequence corresponding to SEQ ID NO: 1, the epitope corresponding to a solvent exposed, antibody accessible knuckle region of oligomeric Aβ.

In another embodiment of the invention, there is provided antibodies that are capable of binding a cyclic peptide derived from Aβ, the cyclic peptide comprising a conformational epitope having an amino acid sequence of at least SNK, and corresponding to a solvent exposed, antibody accessible knuckle region of oligomeric Aβ.

In a further embodiment of the invention, there is provided antibodies that are capable of binding a cyclic peptide derived from Aβ, the cyclic peptide comprising a conformational epitope having an amino acid sequence corresponding to SEQ ID NO: 1, and corresponding to a solvent exposed, antibody accessible knuckle region of oligomeric Aβ.

In certain embodiments, such antibodies may bind oligomeric forms of Aβ with greater affinity than non-oligomeric forms of Aβ.

In another embodiment, there is provided a method of treatment of a subject having or suspected of having Alzheimer's disease, the method comprising administering to the subject a therapeutically effective amount of an antibody that is capable of binding to a cyclic peptide derived from Aβ, where the cyclic peptide comprises a conformational epitope having an amino acid sequence of at least SNK corresponding to a solvent exposed, antibody accessible knuckle region of oligomeric Aβ. In certain embodiments, the antibody may bind oligomeric forms of Aβ with greater affinity than non-oligomeric forms of Aβ.

In another embodiment, there is provided a method of preventing the development or progression of AD in a subject, the method comprising administering to the subject a therapeutically effective amount of an antibody that is capable of binding to a peptide that specifically bind a cyclic peptide derived from Aβ, where the cyclic peptide comprises a conformational epitope having an amino acid sequence of at least SNK corresponding to a solvent exposed, antibody accessible knuckle region of oligomeric Aβ. In certain embodiments, the antibody may bind oligomeric forms of Aβ with greater affinity than non-oligomeric forms of Aβ.

Further aspects of the invention will become apparent from consideration of the ensuing description of preferred embodiments of the invention. A person skilled in the art will realize that other embodiments of the invention are possible and that the details of the invention can be modified in a number of respects, all without departing from the Inventive concept. Thus, the drawings, descriptions and examples are to be regarded as illustrative in nature and not restrictive.

EXAMPLES

Example 1: Aβ Purification and Aggregation and Oligomer Characterization

Transformation, Expression and Purification

E. coli BL21 (DE3) pLysS cells and E. coli DH5α cells were transformed with a construct encoding Aβ 1-40. E. coli cells from 1 L culture were resuspended in 25 mL lysis buffer (50 mM TrisHCl pH 8.0+1 mM ethylene diamine tetraacetic acid (EDTA)) to obtain a homogenized suspension (no protease inhibitors were added). The suspension was transferred to a 40 mL centrifugation tube (JA-20), put on ice and subjected to sonication for a period of 3 min at intensity 6 (i.e. the maximum setting for a small sonicator tip) and 50 HZ intermittence, followed by a centrifugation step of 10 min at 18000 g at 4° C. This sonication process was repeated 3 times. The soluble fractions were recovered each time and analyzed via SDS-PAGE (TCA precipitation was not necessary in this case). Finally, the pellet was resuspended in 12.5 mL buffer containing 8M urea, 10 mM TrisHCl pH 8.0, 1 mM EDTA, followed by one additional sonication step and a centrifugation step (18000 rpm for a period of 10 min). Subsequently, this solution was diluted 4 times (addition of 37.5 mL) with 10 mM Tris pH 8.0 mM EDTA. This protein solution was then incubated with DEAE-cellulose (D52 from Whatman; this was first regenerated with 0.5 N NaOH for a period of 15 min, followed by a water wash and 0.5 M HCl, followed by several water washes and finally a concentrated buffer solution (50 mM Tris pH 8.0+1 mM EDTA)) that was finally equilibrated with the actual buffer for purification (25 mM Tris pH 8.0+1 mM EDTA). The peptide was allowed to bind to the resin in batch under gentle shaking conditions (i.e. in a falcon tube with a magnet inside, placed on magnetic stirring plate) for a periods of 20 min. The unbound proteins was collected in the flow through, after centrifugation for a period of 1 min at 1200 rpm to sediment the beads. These beads were removed with a pipette.

Several washes were carried out, each with a 5 min incubation time and a short centrifugation step (1 min at 1200 rpm) to remove the fractions: 25 mM TrisHCl pH 8.0+1 mM EDTA with respectively 0, 50, 75, 100, 125, 150, 200, 250, 300, 500 mM NaCl were used. The eluted fractions were kept on ice to preserve the monomeric state of the peptides.

With this approach, 250 uL of the collected fractions were analyzed by SDS-PAGE after TCA precipitation. For TCA precipitation, samples were incubated in 20% trichloroacetic acid (TCA) for at least 30 min on ice, then centrifuged for 15 min at 14,000 rpm. Supernatant was discarded and the pellet was washed with 750 uL ice cold acetone, then centrifuged for a 5 min period at 14,000 rpm. Acetone was removed and the remnants were left to evaporate. The pellet was re-dissolved with protein loading dye and analyzed 8-10 uL on SDS-PAGE.

Aβ Aggregation Protocol and Oligomerization of Aβ

To achieve monomerization of Aβ, purified Aβ was dialysed against milliQ water and lyophilized. After lyophilisation, the Aβ was recovered in one of TCA or formic acid and was then evaporated to form a monomer molecular layer on a glass tube. The monomeric Aβ was re-suspended in PBS (5 mM) at a pH of about 6.8 to maintain Aβ in the monomeric form.

To achieve oligomerization of Aβ, monomeric Aβ was used as a starting material and was incubated at 200 µM under sonication for a period of 12 hours at 33° C. This procedure leads to the formation of Aβ oligomers rather Aβ fibrils.

Characterization of Oligomers

The size of oligomer was characterized by dynamic light scattering (DLS), a well-known technique which may be used to determine the size distribution profile of particles in suspension. Where the light source is a laser, and is monochromatic and coherent, a time-dependent fluctuation in the scattering intensity is observed. These fluctuations are a result of the small molecules in solution are undergoing Brownian motion and therefore the distance between the scatterers in the solution is constantly changing with time. When light hits small particles the light scatters in all directions, known as Rayleigh scattering. This scattered light then undergoes either constructive or destructive interference by the surrounding particles and within this intensity fluctuation, information is contained about the time scale of movement of the scatterers. DLS was used to determine the size distribution of the Abeta sample in solution, and to confirm whether Abeta was in a monomeric or oligomeric form.

FIG. 1 illustrates that the Aβ sample analyzed using DLS was monomeric Aβ. Commercially available Aβ(1-40) (50 µM) was incubated in 5 mM PBS at 10° C. A hydration radius (Rh) of less than 1 nm was calculated. These results are consistent with an expected Rh of less than about 1 nm for monomeric Aβ that would be known by a person skilled in the art to be typical of monomeric Aβ.

Figure 2:
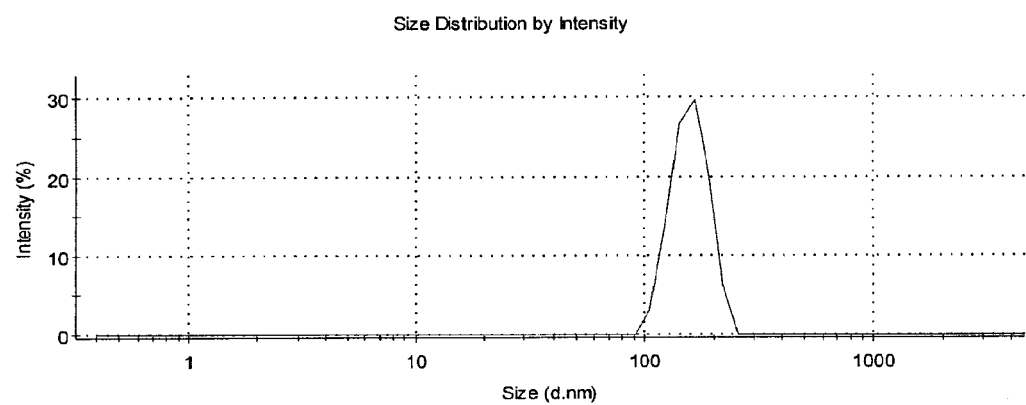
FIG. 2 graphically illustrates the results of dynamic light scattering which show the dynamic properties of oligomeric Aβ.

FIG. 2 illustrates that the Aβ sample analyzed using DLS was oligomeric Aβ. Commercially available Aβ(1-40) (80 µM) was incubated in 150 mM PBS at 10° C. The results indicate a quasi monodisperse population. A hydration radius (Rh) of 200 nm was calculated. The results are consistent with an expected Rh between about 100 nm-200 nm for oligomeric Aβ that would be known by a person skilled in the art to be typical of oligomeric A.

Figure 3:
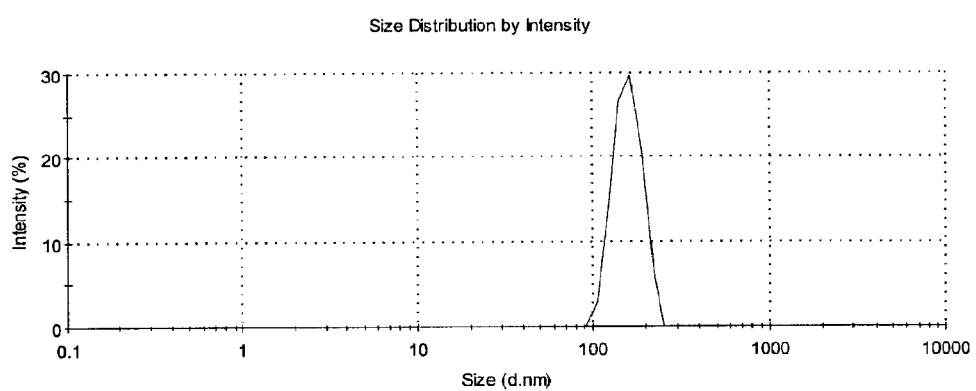
FIG. 3 graphically illustrates the results of dynamic light scattering show the dynamic properties of oligomenc Aβ.

FIG. 3 illustrates that the Aβ sample analyzed using DLS was oligomeric Aβ. Commercially available Aβ(1-40) (50 µM) was incubated in 150 mM PBS at 10° C. The results indicate a quasi monodisperse population. A hydration radius (Rh) of 190 nm was calculated. The results are consistent with an Rh typical of oligomeric A.

Example 2: Production of Cyclic Peptide Comprising a Conformationally Constrained Epitope A cyclic peptide comprising the novel conformational epitope was constructed in a constrained loop conformation using a disulfide linkage between cysteines residues located at the N- and C-termini of this peptide. Two non-native cysteines were added to the GSNKG sequence, one at the C-terminus and one at the N-terminus. The two cysteines were oxidized under controlled conditions to form a disulfide bridge.

The structure of the cyclic peptide was configured to mimic the "knuckle" conformation and orientation of the knuckle region in Aβ oligomers comprising the novel conformational epitope.

FIG. 4 illustrates a three-dimensional model of the disulfide-cyclized peptide comprising the novel conformational SNK epitope.

A person of skill in the art would under-stand that other methods of forming a constrained epitope are known in the field. For example, a peptide may be cyclized by formation of a bond between two residues of the peptide, providing a closed loop. Cyclic peptides may be described as homodetic (where all bonds are peptide bonds) or heterodetic (where there are both peptide bonds, and other types of bonding, such as ester, ether, amide or disulfide linkages within the cyclic peptide). Peptides may be cyclized using chemical or enzymatic methods. US Patent Publication 2009/0215172 describes recombinant proteins that catalyze the head to tail cyclization of peptides via amide bonds, in a manner independent on the sequence of the peptide. Recognition sequences in a prepeptide surrounding the peptide of interest dictate the cyclization. Bourne et al (Methods in Molecular Biology, 2005 298:151-166) describes combinatorial methods for preparation of an array of cyclic peptides via use of a safety catch linker and a sorted procedure. US Patent publication 2004/0014100 discloses a method for in vivo production of cyclic peptides. US Patent publication 2010/0240865, US Patent Publication 2010/0137559, and U.S. Pat. No. 7,569,541 describe various methods for cyclization of peptides for example, peptides may be cyclized via oxidation of thiol- or mercaptan-containing residues at the N-terminus or C terminus, or internal to the peptide. Examples of thiol-containing residues include cysteine, homocysteine, penicillamine. In some embodiments a first thiol-containing residue is cysteine; in some embodiments both a first and a second thiol-containing residue are cysteine. The two thiol-containing residues within the peptide may be oxidized to form a dimeric amino acid cysteine, linked by a disulphide bond. A variety of oxidative reagents may be used to accomplish such a thiol-disulfide converstion, for example, oxygen (air), dimethyl sulphoxide, oxidized glutathione, potassium ferricyanide, thallium(III) trifluoro acetate, or other oxidative reagents such as may be known to those of skill in the art and used with such methods as are known to those of skill in the art. Examples of such methods are described in PCT Publication WO01/92466, and Andreu et al., 1994. Methods in Molecular Biology 35:91-169.

Example 3: Derivation and Screening Aβ Oligomer-Specific Monoclonal Antibodies

Monoclonal antibodies (mAbs) to the Aβ oligomer-specific conformational epitope (SEQ ID NO: 1) were generated by producing an antibody directed to an epitope constrained in a loop conformation using disulfide linkage between cysteines at the N- and C-termini of this peptide as described in Example 2.

BALB/C mice were immunized with the novel constrained loop epitope (CLE), referred to here as the GSNKG-CLE, linked to multiple antigen peptide (MAP) or Keyhole Limpet Hemocyanin (KLH), which have been used for PrP and SOD1-misfolding specific epitopes (Paramithiotis et al, 2003; Rakhit et al, 2007). Mouse sera were screened on GSNKG-CLE linked to bovine serum albumin (BSA), and spleen fusion and hybridoma screening was performed on those mice with specific and strong interaction with GSNKG-CLE and not unstructured soluble Aβ. Positive selected IgG-secreting clones were subjected to large-scale production and subsequent characterization by immunological methods with cyclic and linear GSNKG-BSA, synthetic Aβ oligomers and with AP oligomers derived from AD brain.

Monoclonal antibodies (mAb) were generated against cyclic GSNKG peptides and pre-screened for binding by peptide ELISA. Some antibodies generated against GSNKG cyclic peptides preferentially recognized cyclic peptides, some linear peptides, and some both cyclic and linear. The ability of antibodies to recognize both linear and cyclic peptide may for example, relate to immune recognition of a cyclic peptide that had been partially or completely linearized by reduction of the cysteine bridge in vivo. Antibodies generated to intermediate-GSNKG peptides represent antibodies that recognize both cyclic and linear peptide. Based on the ELISA results, two cyclic-specific antibodies (5D8, 5E3), two linear-specific (3F5, 3G2), and two intermediate-specific (4D11, 4D12) IgG clones were chosen for further analysis. A Biacore™ platform, a technology that utilizes optical phenomenon of surface plasmon resonance to monitor biomolecular interactions in real time and without the need for labelling, was used for further analysis.

Figure 5:
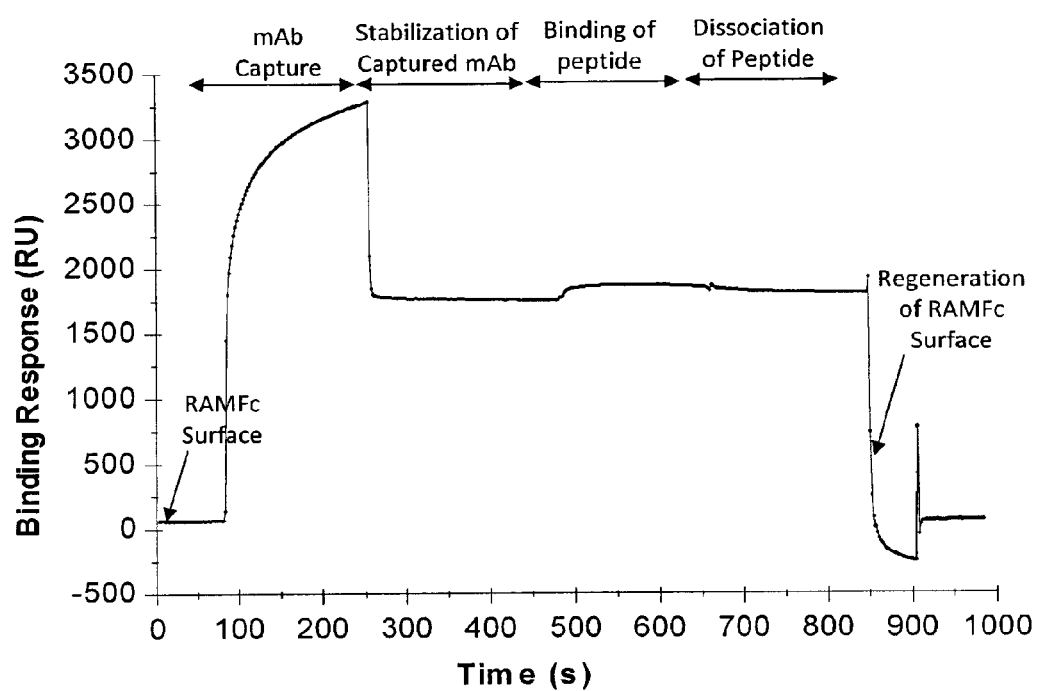
FIG. 5 graphically illustrates the Biacore™ results of a representative analytical cycle for screening of anti-SNK monoclonal antibody binding to a conformational peptide comprising SNK.

FIG. 5 depicts exemplary Biacore™ results. Monoclonal antibodies were captured from tissue culture supernatants using a rabbit anti-mouse Fc-specific (RAMFc) antibody which was covalently immobilized on a CM5 sensorchip. Binding of BSA-conjugated GSNKG peptides (linear and cyclic) and oligomeric Aβ(1-42) was then examined by flowing these analytes over the captured mAb. Binding responses were referenced against a flow cell that contained immobilized RAMfc but no captured mAb, and further blanked with sample diluent that consisted of Hepes Buffered Saline (HOS) containing 1 mg/ml carboxymethyl dextran. Additionally, the observed responses were normalized against the amount of mAb captured, to accurately allow for the comparisons across the different mAbs.

Figure 6:
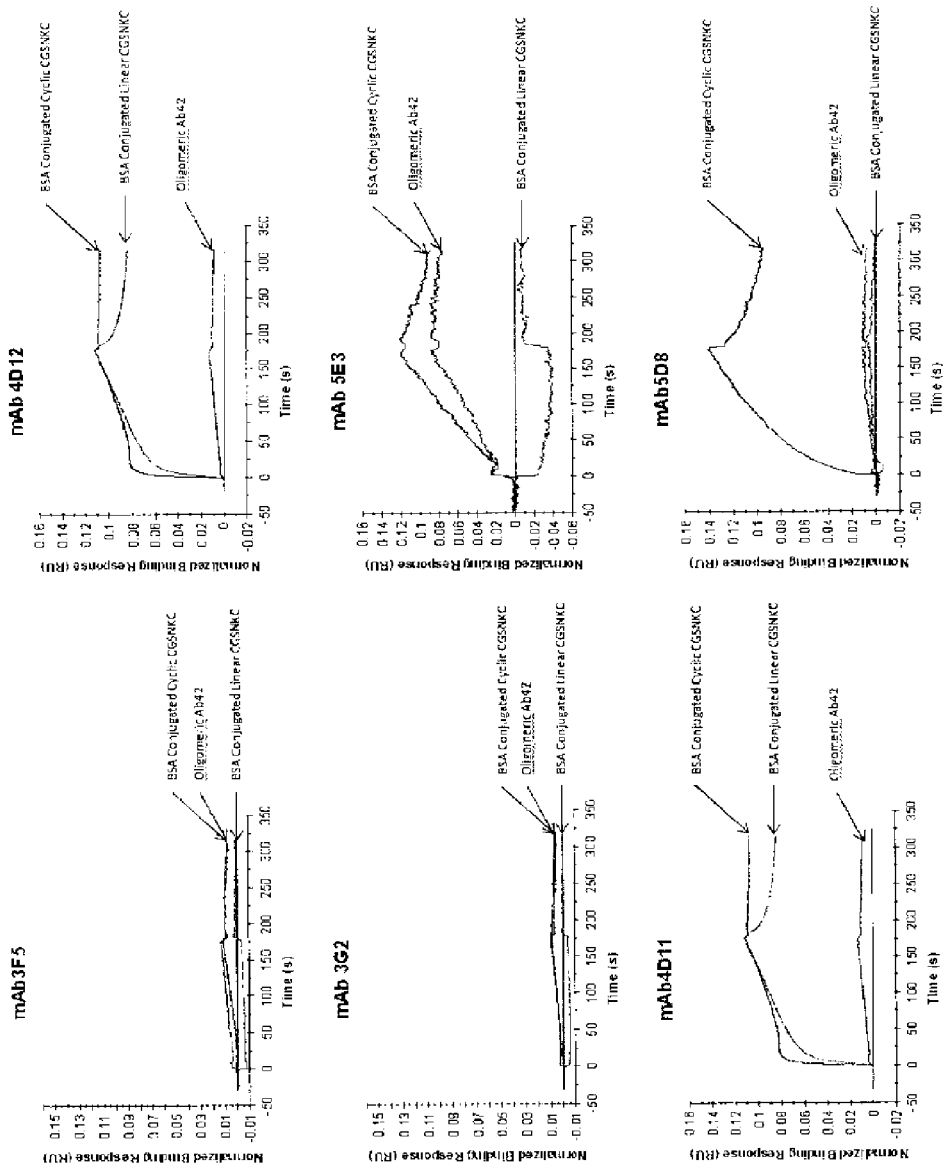
FIG. 6 graphically illustrates the results of Biacore™ sensorgram overlays which shows the binding of BSA-conjugated linear or cyclic peptides comprising the SNK epitope to linear (3F5, 3G2), cyclic (5E3, 5D8) and intermediate-specific (4D11, 4D12) monoclonal antibodies, and reactivity of these antibodies to synthetic Aβ 1-42 oligomers.
Figure 7:
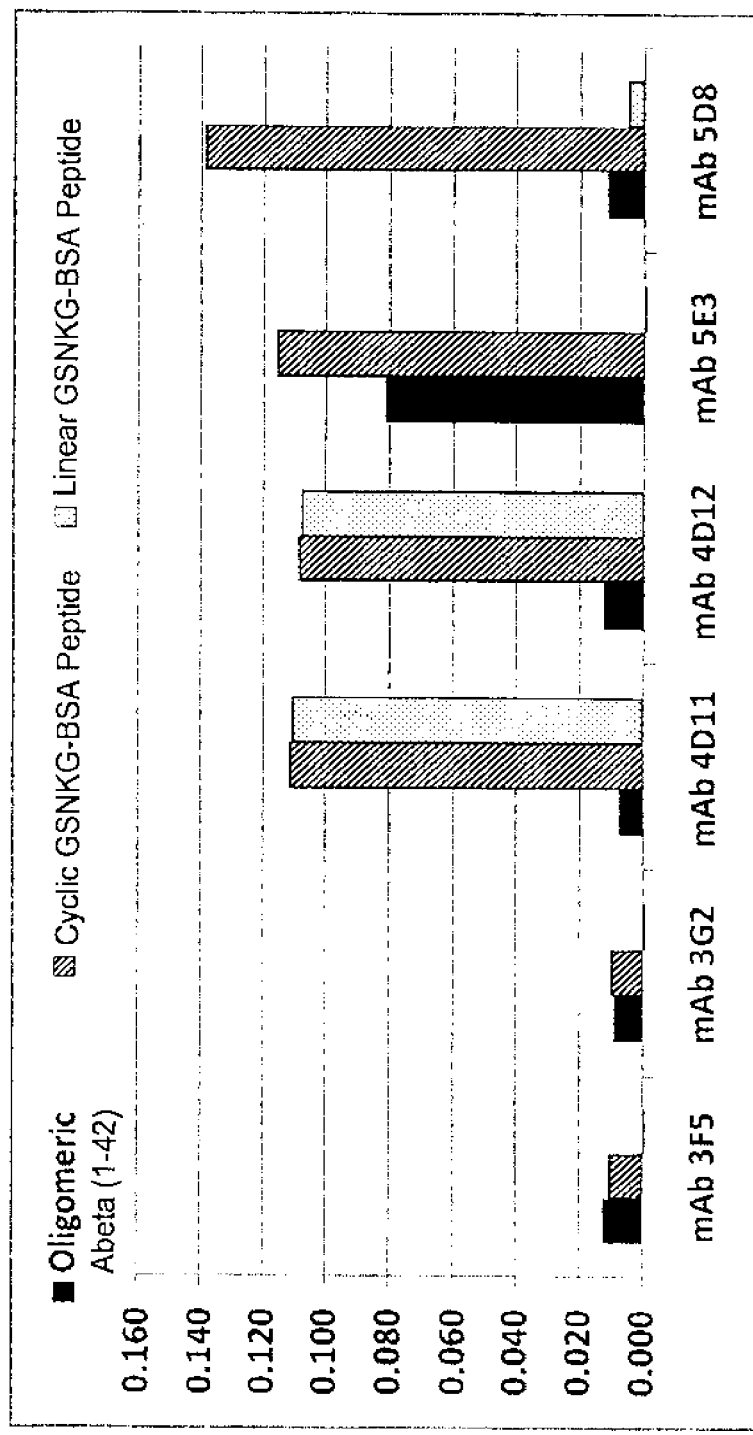
FIG. 7 graphically illustrates the results of Biacore™ sensorgram overlays which shows the binding of BSA-conjugated linear or cyclic peptides comprising the SNK epitope to linear (3F5, 3G2), cyclic (5E3, 5D8) and intermediate-specific (4D11, 4D12) monoclonal antibodies, and reactivity of these antibodies to synthetic Aβ 1-42 oligomers.

FIG. 6 and FIG. 7 depict the resultant Biacore™ sensorgrams, and show that ELISA-selected linear-preferential clones (3F5, 3G2) bound neither linear nor cyclic BSA-coupled peptide on Biacore chips; ELISA-selected intermediate clones (4F11, 4G12) bound to both cyclic and linear peptide on Biacore chips; and the ELISA-selected cyclic clones (5D8, 5E3) bound primarily to cyclic-coupled BSA on Biacore chips. The cyclic clones 5E3 and 5D8 demonstrated the strongest binding to Aβ(1-42) oligomers and cyclic peptides, while also demonstrating little to no binding of the linear peptides as compared to the intermediate clones. The data illustrates the 5E3 antibody demonstrates the greatest binding to Aβ(1-42) oligomers, although both 5E3 and 5D8 bind to the cyclic peptide. These results indicate, in the screening of the antibodies produced using the cyclic peptide of Example 2, a subset of the cyclic-specific antibodies produced preferential antibody recognition of the Aβ oligomer epitope.

Figure 8:
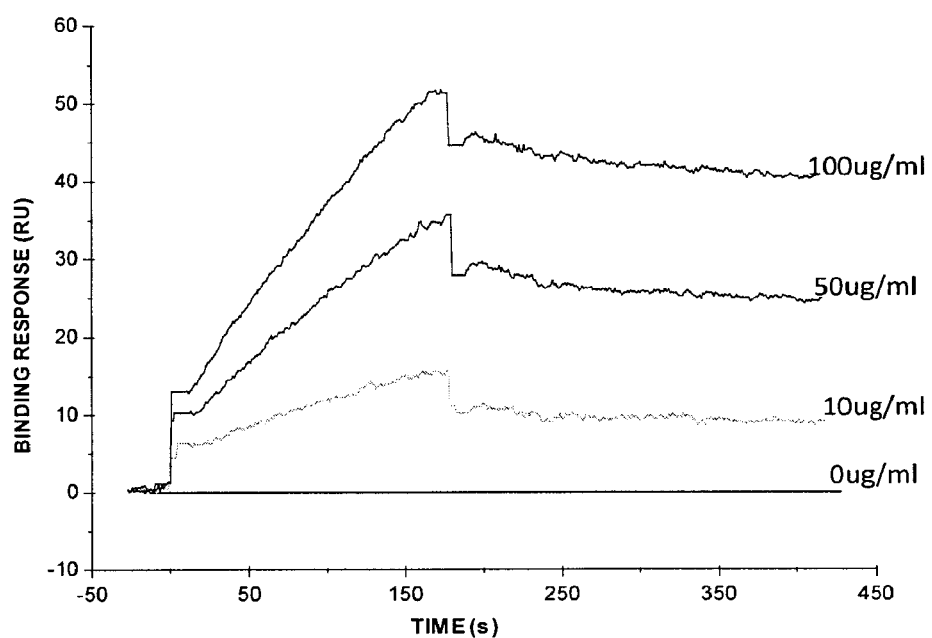
FIG. 8 graphically illustrates the results of Biacore™ analysis which shows the binding to synthetic Aβ1-42 oligomers to cyclic monoclonal antibody 5E3 at varying concentrations.

FIG. 8 shows that mAb 5E3, a cyclic-preferential clone, bound to Aβ (1-42) oligomers in a concentration-dependent manner. This observation demonstrates an accessible and conformationally-constrained epitope in the Aβ oligomers which is titratable, consistent with an authentic immunologic antigen-antibody interaction. Thus the Biacore analyses demonstrate that cyclic-GSNKG peptide and full length oligomeric Aβ (1-42) share a common molecular signature, the conformationally-constrained epitope, which is specifically recognized by the conformationally-sensitive mAb 5E3.

Aβ (1-42) oligomer-specific mAbs may be further tested for therapeutic purpose in cellular and animal models of AD, and for neutralization activity in neurophysiological assays of synaptic function impaired by Aβ oligomers.

Example 4: Flow Cytometry Analyses

A flow cytometry analysis was carried out to determine the degree of antibody binding the APP at the cell surface.

Healthy adult Black/6 mice were euthanized in a carbon dioxide chamber. Brains were removed immediately and perfused in phosphate buffered saline (PBS) followed by submersion in PBS+1% fetal bovine serum (FBS). Single cell suspensions were generated by mincing brains with dissecting scissors and serial passage through 100 μm and 70 μm sieves. Cells were incubated in PBS+1% FBS as a blocking step for 30 min at room temperature. Cells were then incubated (or not) in 100 μl PBS+1% FBS plus either 10 μg/mL, or 1 μg/mL, of 0E10 and 5E3, separately. After 1 h at room temperature cells were washed twice (400×g for 5 min) and resuspended in PBS+1% FBS and anti-mouse antibodies conjugated to either allophycocyanin (APC) or fluorescein (FITC), both at a 1:1000 dilution. In addition to an unstained control, some cells were incubated with secondary antibody alone to control for nonspecific interaction. Secondary antibodies were incubated with sample for 30 min at room temperature after which cells were washed and either analyzed immediately or fixed over night in 4% paraformaldhyde at 4° C. A BD LSRII Flow Cytometer was used to collect data and FlowJo was used for data analysis.

Figure 9:
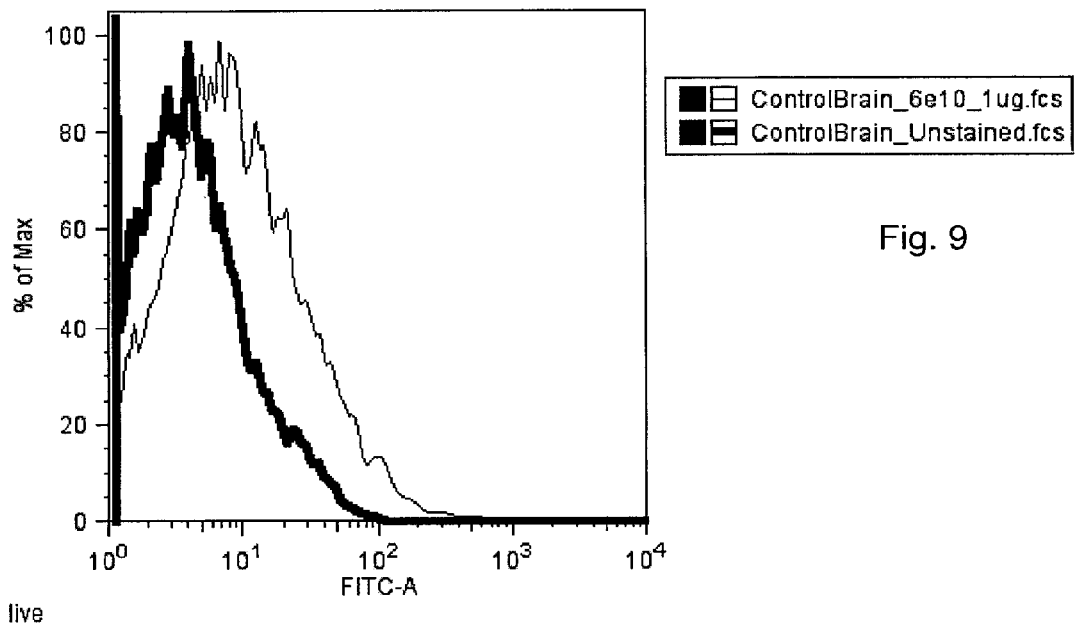
FIG. 9 is a flow cytometry trace which shows the comparison of cells binding labelled 6E10 antibody and a negative control to the APP located at the cell surface.
Figure 10:
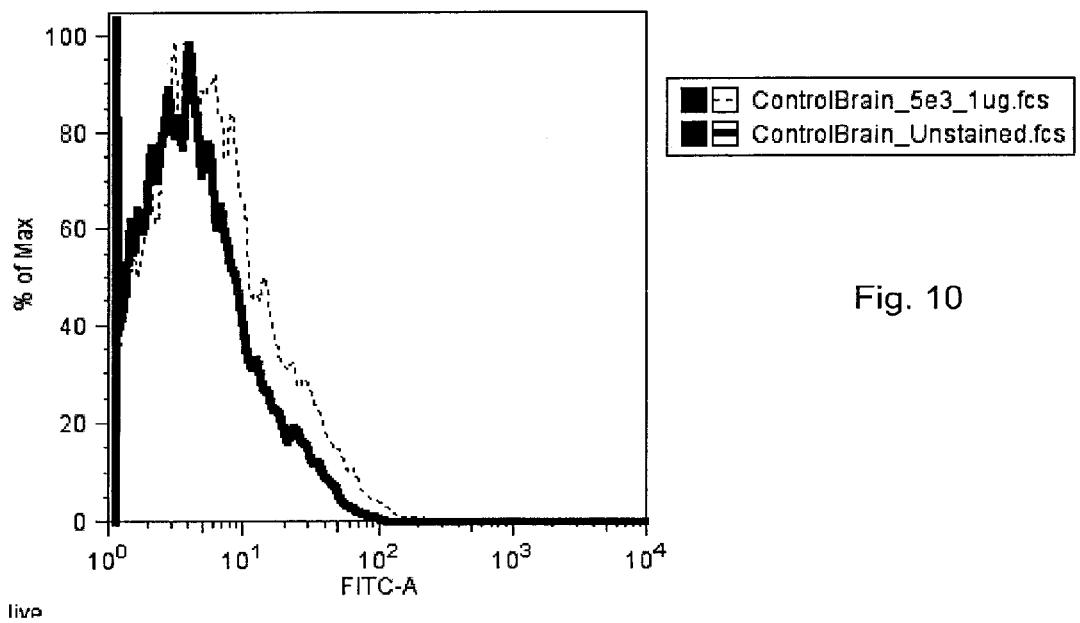
FIG. 10 is a flow cytometry trace which shows the comparison of cells binding labelled 5E3 antibody and a negative control to the APP located at the cell surface.

FIG. 9 and FIG. 10 depict results of the flow cytometry analysis. FIG. 9 is a flow cytometry trace which shows the comparison of cells binding labelled 6E10 pan-Aβ antibody and a secondary antibody negative control to the APP located at the cell surface. FIG. 10 shows the comparison of cells binding labelled 5E3 antibody and a secondary antibody negative control to the APP located at the cell surface. The 6E10 antibody shown in FIG. 9 illustrates a significant proportion of the cells binding FITC labelled 6E10 to APP located at the cell surface. In contract, the 5E3 antibody shown in FIG. 10 illustrates that there is very little binding of FITC labelled 5E3 to the cells as compared to the control. These results clearly illustrates that FITC labelled 5E3 shows significantly less binding of to APP at the cell surface as compared to FITC labelled 6E10. The results of these analyses indicate that the structurally constrained oligomer-specific novel conformational epitope is not present at the cell surface of neurons which is consistent with a linear unstructured nature of the GSNKG motif in native APP. The absence of the structurally constrained novel conformational epitope at the cell surface indicates that an immune response against the cyclic epitope used in treatment of Alzheimer's disease does not target native APP. These results demonstrate that antibodies that specifically bind to the cyclic- GSNKG epitope of oligomeric Aβ have a preferred safety profile as compared to the known 6E10 antibody.

Example 5: Neuronal Analyses

A neuronal toxicity analysis was carried out to determine the degree of cell survival for cells incubated with a mock (media alone) control, soluble (linear), and oligomeric Aβ1-40 in the presence and absence of 5E3 antibody at different concentrations. The mock control was treated with media alone (no antibody).

96 wells containing 10,000 rat primary neurons/well were grown in a poly-L-lysine (ScienCell #0403; 2 micrograms/cm2, 1 hr, 37 degree Celsius, washed 3× with PBS) treated well of a 96-well plate, with 0.2 ml neuronal medium (ScienCell #1521) in each well. The culture medium was changed every day for 7 days. Soluble and oligomeric Aβ(1-40) were incubated 4 hours in the absence or in the presence of the 5E3 antibody at different concentrations (see FIG. 11) in neuronal medium at room temperature in a rotating device. 0.2 ml of this mixture was added to the neurons after removal of the medium. After a period of 24 hrs, cell survival was measured using a Roche Cell Proliferation kit II (#11465015001) according to the manufacturer's protocol. Optical densities were determined with a plate reader.

Figure 11:
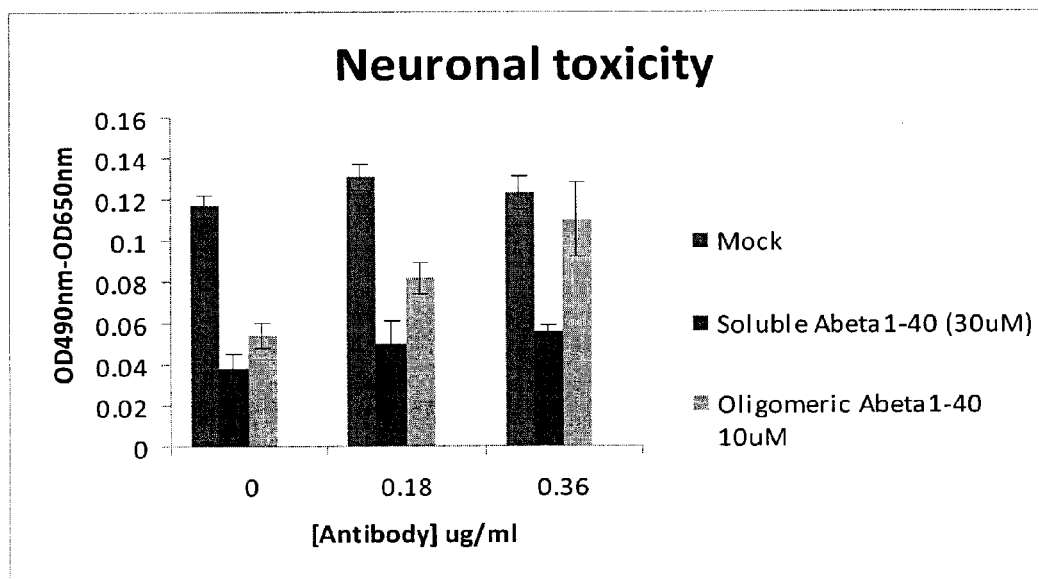
FIG. 11 graphically illustrates the results of a neuronal toxicity analysis which shows the degree of cell survival for cells incubated with a mock control, soluble monomeric and oligomeric Aβ 1-40 in the presence and absence of 5E3 antibody at different concentrations.

FIG. 11 illustrates the results of neuronal toxicity assays. Aβ is toxic to neurons in both the linear Aβ monomer configuration and the oligomeric Aβ configuration. The antibody 5E3 directed against the conformationally constrained Aβ epitope was shown to be protective against oligomeric forms of Aβ. Antibody 5E3 was not shown to be protective for the linear Aβ. These results demonstrate the conformational specificity of the binding of antibody 5E3.

Example 62: Immunoblot Analyses

An immunoblot analysis was conducted to determine the relative binding of 6E10 antibody and 5E3 antibody to APP, monomeric Aβ and oligomeric Aβ.
Homogenization
Brain tissue samples were weighed and subsequently submersed in a volume of fresh, ice cold TBS (supplemented with 5 mM ethylene glycol tetraacetic acid (EGTA), 5 mM EDTA and protease inhibitor cocktail) such that the final concentration of brain tissue was 20%. Tissue was homogenized in this buffer using a mechanical homogenizer as follows: tissue was subjected to homogenizer 3 times for a period of 30 sec each with a period of 30 sec on ice between homogenizations. TBS homogenized samples were then subjected to ultracentrifugation (70,000×g for 90 min). Supernatants were collected and stored at −80° C.

Protein concentration of TBS homogenates was determined using the BCA protein assay. In some cases, an equal amount of protein was fractionated by SDS-PAGE using Tris-Tricine 4-20% gels after boiling in Tris-Tricine Sample Buffer (Invitrogen) and transferred to 0.2 µm polyvinylidene fluoride (PVDF) membranes. After transfer, membranes were submersed in PBS and boiled 2 times for a period of 3 min each for epitope heat recovery. Membranes were subjected to immunoblotting using either 0E10 or the oligomer specific antibody 5E3 as the primary antibody. Both were used at a concentration of 1 ug/ml.

Figure 12:
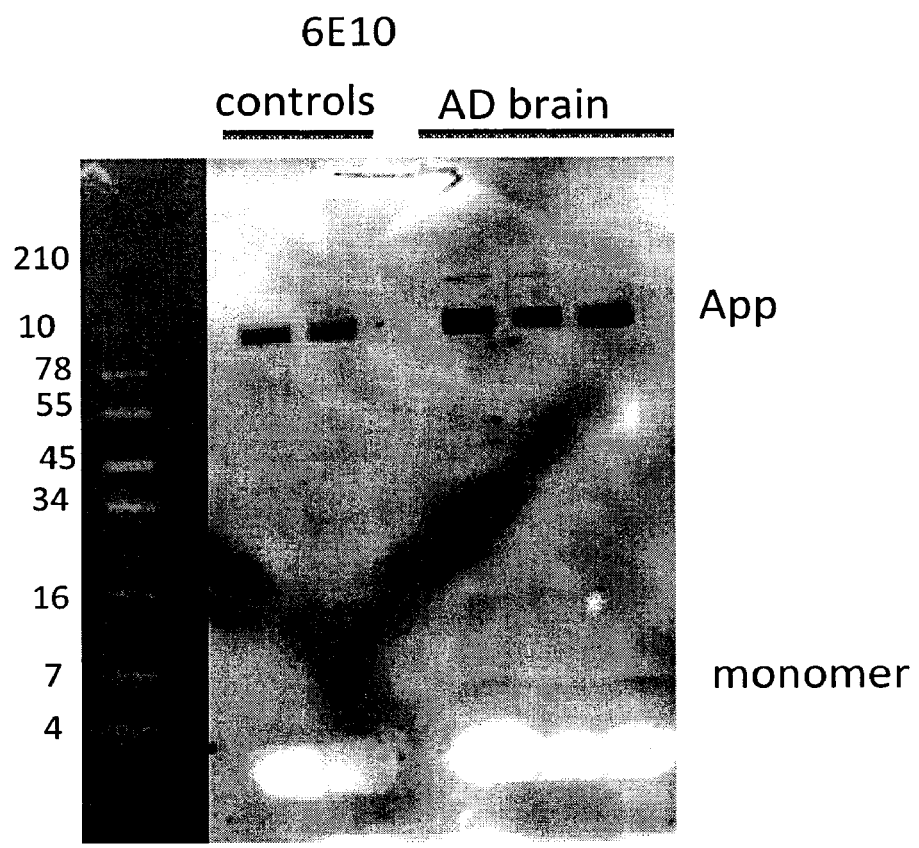
FIG. 12 illustrates the results of an immunoblot which shows brain tissue homogenized in TBS, fractioned in Tris-Tricine gels, and immunoblotted with pan-Aβ 6E10 antibody.

FIG. 12 illustrates the results of an immunoblot which shows brain tissue homogenized in TBS, fractioned in Tris-Tricine gels, and immunoblotted with pan-Aβ 6E10 antibody. Reaction with APP and with monomeric forms of Aβ is evident, as well as minor reactivity to the Aβ oligomer bands.

Figure 13:
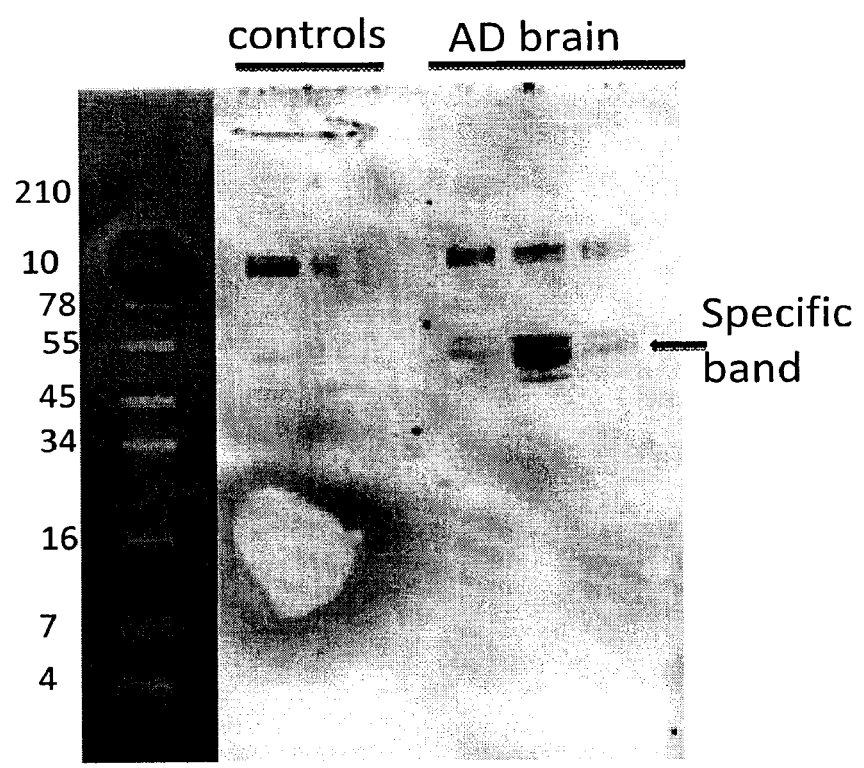
FIG. 13 illustrates the results of an immunoblot which shows brain tissue homogenized in TBS, fractioned in Tris-Tricine gels, and immunoblotted with 5E3 antibody.

FIG. 13 illustrates the results of an immunoblot for antibody 5E3. Antibody 5E3 specifically recognized oligomer species of about 45-55 kDa, apparently SDS stable, indicating strong non-covalent interaction of Aβ monomers in the oligomer species. No reaction with the monomeric form of Aβ was observed, although some limited reactivity with APP is evident on this immunoblot that is presumed to be associated with denaturation and partial native and non-native renaturation on the blot membrane. The pan-Aβ antibody 6E10 showed limited or no recognition of the oligomer species. The Biacore™ data discussed in Example 3 (based on an empirical Biacore™ formula and assuming the stoichiometry between 5E3 and AB42 is 1) is in agreement with the immunoblot, and indicates that the species of Aβ (1-42) that binds to 5E3 to be between a decamer and a tridecamer; given a molecular weight of 4.0-4.3 kDa per monomer, the Biacore data predict an oligomer species of ~50 kDa, consistent with the molecular weight of the major bands detected by the 5E3 mAb.

Example 7: Analysis of Inhibition of Aβ Oligomer Formation

An analysis of Aβ inhibition was conducted to determine the ability of the 5E3 antibody to induce a delay in the propagation of Aβ oligomers.

Static light scattering (SLS) is a technique in physical chemistry that measures the intensity of the scattered light to obtain the average molecular weight (Mw) of a macromolecule like a polymer or a protein. Measurement of the scattering intensity at many angles allows calculation of the root mean square radius, also called the radius of gyration (Rg). By measuring the scattering intensity for many samples of various concentrations, the second virial coefficient A2, can be calculated. For static light scattering experiments, a high intensity monochromatic light, usually a laser, is launched in a solution containing the macromolecules. One or many detectors are used to measure the scattering intensity at one or many angles (θ) at a given wavelength (λ).

In order to measure the weight average molecular weight directly, without calibration, from the light scattering intensity, the laser intensity, the quantum efficiency of the detector and the full scattering volume and solid angle of the detector needs to be known. Since this is impractical, all commercial instruments are calibrated using a strong, known scatterer like toluene since the Rayleigh Ratio of toluene and a few other solvents were measured using an absolute light scattering instrument.

Figure 14:
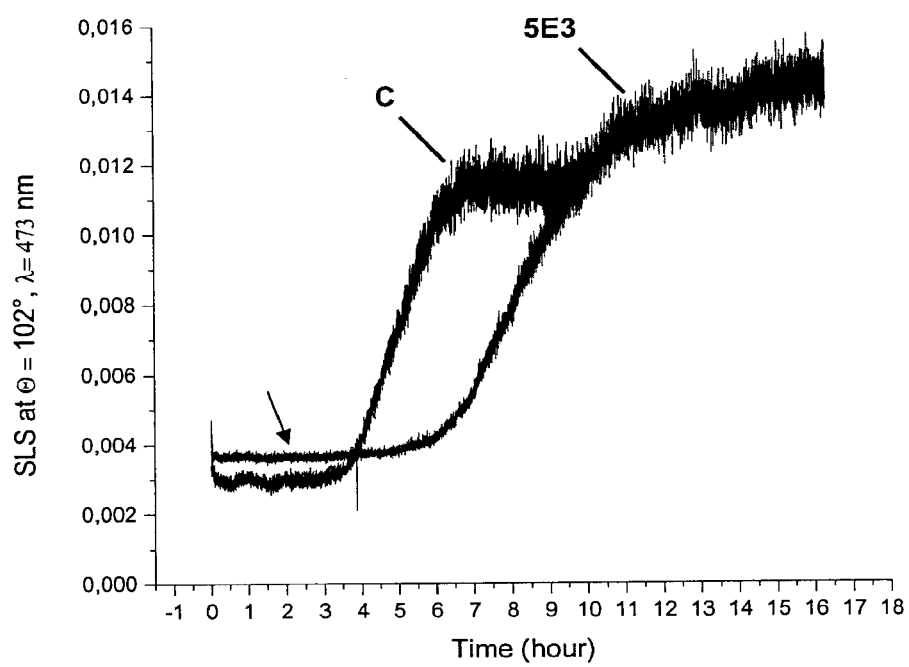
FIG. 14 depicts results of static light scatter experiments to test Aβ polymerization in the presence ("5E3") or absence ("C") of antibody 5E3.

FIG. 14 illustrates the ability of 5E3 antibody to delay the aggregation of monomer Aβ into the toxic oligomer Aβ form. Aβ oligomer formation was tested in the absence of 5E3 ("C" in FIG. 14) or in the presence of 5E3 ("5E3" in FIG. 14). Commercially sourced Aβ(1-40) (23 µM) was incubated at 39° C. in a reaction volume of 150 µL, with antibody 5E3 (2.0 mcM) The shift on the SLS intensity indicate by the arrow correspond to the contribution of 5E3 antibody to the scattered intensity, FIG. 14 illustrates that incubation with antibody 5E3 results in a significant delay in Aβ oligomer formation.

This inhibitory effect on polymerization is supportive of a therapeutic role for antibody 5E3, humanized and chimeric antibodies related thereto, and for the novel conformation epitope itself, for example in a vaccine composition.

Example 8: Detection of Aβ Oligomers in Biological Samples

It is envisaged that purified 5E3 antibody could be used to detect Aβ oligomers in biological samples, such as homogenates from tissue, including brain. This detection could be carried out using a variety of detection platforms, including the Biacore™ platform, and could have diagnostic and/or prognostic value.

Example 9: Treatment with 5E3 and Related Antibodies & Vaccines

Treatment with 5E3 antibodies could serve to specifically and/or selectively clear toxic Aβ oligomers, and may be useful in treating and/or preventing onset or progression of diseases related to Aβ oligomer toxicity, such as Alzheimer's disease. Human or humanized antibodies directed to the same epitope as 5E3 would be useful for treating and/or preventing Alzheimer's disease. In another aspect, an epitope overlapping that epitope recognized by 5E3 would be useful for treating and/or preventing Alzheimer's disease.

Similarly, the novel conformational epitope described herein would likely be useful in eliciting a specific immune response to Aβ oligomer, which would be useful for treatment or prevention of, for example, in Alzheimer's disease.

The above-described embodiments are intended to be examples only. Alterations, modifications and variations can be effected to the particular embodiments by those of skill in the art without departing from the scope, which is defined solely by the claims appended hereto.

REFERENCES

Gelinas, D. S., et al., Immunotherapy for Alzheimer's disease. Proc Natl Acad Sci USA, 2004. 101 Suppl 2: p. 14657-62.
Robinson, S. R., et al., Lessons from the AN 1792 Alzheimer vaccine: lest we forget. Neurobiol Aging, 2004. 25(5): p. 609-15.
Broytman, O. and J. S. Malter, Anti-Abeta: The goad, the bad, and the unforeseen. J Neurosci Res, 2004. 75(3): p. 301-6.
Mathews, P. M. and R. A. Nixon, Setback for an Alzheimer's disease vaccine: lessons learned. Neurology, 2003. 61(1): p. 7-5.
Gani, F. and E. M. Sigurdssan, New directions towards safer and effective vaccines for Alzheimer's disease. Curr Opin Mol Ther, 2005. 7(1): p. 17-23.
Jung, S. S., J. Nalbantoglu, and N. R. Cashman, Alzheimer's beta-amyloid precursor protein is expressed on the surface of immediately ex vivo brain cells: a flow cytometric study. J Neurosci Res, 1996. 40(3): p. 336-48.
Jung, S. S., S. Gauthier, and N. R. Cashman, Beta-amyloid precursor protein is detectable on monocytes and is increased in Alzheimer's disease. Neurobiol Aging, 1999. 20(3): p. 249-57,
Morimoto, T., et al., Involvement of amyloid precursor protein in functional synapse formation in cultured hippocampal neurons. J Neurosci Res, 1998, 51(2): p. 185-95.
Mileusnic, R., C. L. Lancashire, and S. P. Rose, Amyloid precursor protein: from synaptic plasticity to Alzheimer's disease. Ann N Y Acad Sci, 2005. 1048: p. 149-65.
Mileusnic, R., et al., APP is required during an early phase of memory formation. Eur J Neurosci, 2000. 12(12): p. 4487-95.
Lambert, M. P., et al., Monoclonal antibodies that target pathological assemblies of Abeta. J Neurochem, 2007. 100(1): p. 23-35.
Lacor, P. N., et al., Abeta oligomer-induced aberrations in synapse composition, shape, and density provide a molecular basis for loss of connectivity in Alzheimer's disease. J Neurosci, 2007. 27(4): p. 796-807.
Ronicke, R., et al., Abeta mediated diminution of MTT reduction—an artefact of single cell culture? PLoS One, 2008, 3(9): p. e3236,
Balducci, C., et al., Synthetic amyloid-beta oligomers impair long-term memory independently of cellular prion protein. Proc Natl Acad Sci USA. 2010, 107(5): p. 2295-300.
Shenker, G. M., et al., Amyloid-beta protein dimers isolated directly from Alzheimer's brains impair synaptic plasticity and memory. Nat Med, 2008. 14(8): p. 837-42.
Selkoe, D. J., Soluble oligomers of the amyloid beta-protein impair synaptic plasticity and behavior. Behav Brain Res, 2008. 192(1): p. 106-13.
Klyubin, I., et al., Amyloid beta protein immunotherapy neutralizes Abeta oligomers that disrupt synaptic plasticity in vivo. Nat Med, 2005. 11(5): p. 556-61.
Walsh, D. M., et al., Naturally secreted oligomers of amyloid beta protein potently inhibit hippocampal long-term potentiation in vivo. Nature, 2002. 416(6880): p. 535-9.
Wang, N. W., et al., Soluble oligomers of beta amyloid (1-42) inhibit long-term potentiation but not long-term depression in rat dentate gyrus. Brain Res, 2002. 924(2): p. 133-40.
Lesne, S., et al., A specific amyloid-beta protein assembly in the brain impairs memory. Nature, 2006. 440(7082): p. 352-7.
Lauren, J., et al., Cellular prion protein mediates impairment of synaptic plasticity by amyloidbeta oligomers. Nature, 2009. 457(7233): p. 1128-32.
Luhrs, T., et al., 3D structure of Alzheimer's amyloid-beta (1-42) fibrils. Proc Natl Acad Sci USA, 2005. 102(48): p. 17342-7.
Rauk, A., Why is the amyloid beta peptide of Alzheimer's disease neurotoxic? Dalton Trans, 2008 (10): p. 1273-82.

What is claimed is:

1. An antigenic peptide comprising a conformational epitope having a constrained cyclic configuration, wherein the conformational epitope has an amino acid sequence of at least SNK corresponding to a solvent-exposed, antibody accessible knuckle region of oligomeric Aβ, and wherein the K (Lysine) is solvent-exposed.

2. The antigenic peptide of claim 1, wherein the conformational epitope has an amino acid sequence corresponding to SEQ ID NO: 1.

3. The antigenic peptide of claim 1 or claim 2, wherein the solvent-exposed, antibody accessible knuckle region of oligomeric Aβ corresponds to residues 25 to 29 of oligomeric Aβ (1-40) or residues 25 to 29 of oligomeric Aβ (1-42).

4. The antigenic peptide of claim 1, wherein the antigenic peptide has an amino acid sequence of SEQ ID NO: 8.

5. An immunogenic composition comprising the antigenic peptide of claim 1 and a pharmaceutically acceptable adjuvant.

6. A method of treating or delaying the onset of Alzheimer's Disease in a patient in need of said treatment comprising administering said immunogenic composition of claim 5.

7. An immunogenic composition comprising the antigenic peptide of claim 3 and a pharmaceutically acceptable adjuvant.

8. A method of treating or delaying the onset of Alzheimer's Disease in a patient in need of said treatment comprising administering said immunogenic composition of claim 7.

9. The immunogenic composition of claim 5, wherein the conformational epitope of the antigenic peptide has an amino acid sequence corresponding to SEQ ID NO: 1.

10. A method of treating or delaying the onset of Alzheimer's Disease in a patient in need of said treatment comprising administering said immunogenic composition of claim 9.

11. The immunogenic composition of claim 5, wherein the antigenic peptide has an amino acid sequence corresponding to SEQ ID NO: 8.

12. A method of treating or delaying the onset of Alzheimer's Disease in a patient in need of said treatment comprising administering said immunogenic composition of claim 11.

* * * * *